United States Patent
Vladila

(10) Patent No.: US 10,137,309 B2
(45) Date of Patent: Nov. 27, 2018

(54) SYSTEM AND METHOD FOR PROLIFERATION OF STEM CELLS IN CELLULAR TISSUE

(71) Applicant: Bogdan Constantin Vladila, Bucharest (RO)

(72) Inventor: Bogdan Constantin Vladila, Bucharest (RO)

(*) Notice: Subject to any disclaimer, the term of this patent is extended or adjusted under 35 U.S.C. 154(b) by 720 days.

(21) Appl. No.: 14/492,731

(22) Filed: Sep. 22, 2014

(65) Prior Publication Data

US 2015/0140633 A1 May 21, 2015

Related U.S. Application Data

(63) Continuation-in-part of application No. PCT/EP2013/055941, filed on Mar. 21, 2013.

(30) Foreign Application Priority Data

Mar. 21, 2012 (RO) .................. 2012-00201

(51) Int. Cl.
- *A61N 2/02* (2006.01)
- *A01G 7/04* (2006.01)
- *C12N 13/00* (2006.01)
- *A61N 2/00* (2006.01)

(52) U.S. Cl.
CPC ............... *A61N 2/02* (2013.01); *A01G 7/04* (2013.01); *C12N 13/00* (2013.01); *A61N 2/004* (2013.01)

(58) Field of Classification Search
CPC .......... A61N 2/02; A61N 2/004; A61N 2/002; A61N 2/00; A61N 1/0484; A01G 7/04; C12N 13/00; A61H 2201/10; A61H 39/04; A61H 39/00; A61B 5/6803
See application file for complete search history.

(56) References Cited

U.S. PATENT DOCUMENTS

| 3,915,151 A | 10/1975 | Kraus |
| 4,993,413 A | 2/1991 | McLeod et al. |
| 5,192,263 A * | 3/1993 | Kraus ................ A61N 2/02 600/14 |

(Continued)

FOREIGN PATENT DOCUMENTS

| CA | 1202804 A1 | 4/1986 |
| GB | 1393702 A | 5/1975 |

(Continued)

*Primary Examiner* — Kaylee Wilson
(74) *Attorney, Agent, or Firm* — Hershkovitz & Associates, PLLC; Abe Hershkovitz

(57) ABSTRACT

A method and a system are provided for subjecting organic cells in a region of a subject to an extremely low frequency magnetic field. At least one resonance medium is operably connected to a generator. The generator produces a sinusoidal non-harmonic current signal, having a predetermined frequency of substantially between 7.5 Hz and 7.9 Hz. The resonance medium is energized by the signal and the magnetic field yielded is substantially between 0.7 mT and 3 mT to be located adjacent organic cellular tissue in the region for a predetermined period. Organic cells in the laboratory, repository or in the region are subjected to a constant magnetic field of less than 1 mT and having a frequency of substantially between 7.5 Hz and 7.9 Hz for the predetermined period.

18 Claims, 17 Drawing Sheets

(56) References Cited

U.S. PATENT DOCUMENTS

| | | | |
|---|---|---|---|
| 5,935,054 A | | 8/1999 | Loos |
| 5,951,459 A | * | 9/1999 | Blackwell ................ A61N 2/02 600/13 |
| 2003/0028072 A1 | | 2/2003 | Fischell et al. |
| 2010/0298886 A1 | | 11/2010 | Werner et al. |

FOREIGN PATENT DOCUMENTS

| | | | |
|---|---|---|---|
| JP | 2001026529 | A | 1/2001 |
| WO | 9527533 | A1 | 10/1995 |
| WO | 9611723 | A1 | 4/1996 |
| WO | 2006001644 | A1 | 1/2006 |
| WO | 2012093277 | A2 | 7/2012 |

* cited by examiner

SYSTEM AND METHOD FOR PROLIFERATION OF STEM CELLS IN CELLULAR TISSUE

CROSS-REFERENCE TO RELATED APPLICATIONS

This application is a continuation-in-part of International Application PCT/EP2013/055941, the disclosure of which is incorporated herein in its entirety by reference.

FIELD OF THE INVENTION

The present invention relates to a system for proliferation of stem cells, and to a method using the system for proliferation of stem cells. More particularly, the present invention relates to a system and a corresponding method for the local application of an extremely low frequency (ELF) magnetic field (MF) to stem cells in cellular tissue, wherein the cellular tissue is in vivo or grown in vitro, in repositories or cellular cultures laboratories.

BACKGROUND OF THE INVENTION

Studies performed at research centers such as MIT (Massachusetts Institute of Technology) and the Albert Einstein Medicine College have shown that the application of electromagnetic fields in the form of very low frequency pulses, similar to cerebral waves, leads to an increase of the electric potential at the cell membrane level. This result has beneficial effects, such as impeding the penetration of microbes and viruses within cells and their rate of development within the body, and improving blood circulation which, in turn, improves oxygenation of the cells. Another beneficial effect that has been noted is an improvement in the exchange of calcium ions (Ca+2) resulting from an extracellular influx at the cell level, and an increased body. A summary of such studies in this field has been authored by Richard A. Luben et al in "Effects of electromagnetic stimuli on bone and bone cells in vitro: Inhibition of responses to parathyroid hormone by low-energy low-frequency fields", published in *Proc. Natl. Acad. Sci. USA*, vol. 79, pages 4180-4184, July 1982: Medical Sciences. In this reference, a significant improvement in the healing of compound fractures is described as the result of subjecting same to a pulsating ELF field with a frequency ranging from 10 to 90 Hz.

The use of low frequency is known in the field of stomatology, for increasing the blood circulation inside the gums, for example as disclosed in international patent application WO2006001644. The device described therein consists of a low frequency generator which is connected to the support of a silicone electrode via a cable. The silicone electrode is applied to the gum in the required region for enhancing blood circulation and to assist in suppressing pain.

The main disadvantage of this technique is that, contrary to the desirable effects of the apparatus and method of the present invention, pursuant to which the applied magnetic field should remain undisturbed by applying a constant current without variation, the low frequency in WO2006001644 cannot be applied over extended periods of time.

Another, comparable ELF magnetic or electromagnetic field example is disclosed in Canadian patent application CA 1202804, which describes the use of ELF for correcting positional anomalies of the teeth. The effect provided by this technique assists the repair of the lower and upper jaw soft tissues, by applying some permanent magnets, electromagnets or electromagnetic induction coils subjected to a very low frequency field to a relevant buccal region. The ELF range is produced by the mandible movement interacting with some adjacent electrolytes for outputting a regenerating current.

The main disadvantage of this technique is that the value of the ELF current obtained cannot be constant, nor can it be adjusted as a function of cell treatment requirements, since it depends upon momentary human action.

Japanese patent application JP2001026529 discloses an apparatus with magnets successively supplied with both a low frequency generator and a high frequency generator for cleaning the tophus or the gum, in order to stimulate the lymphatic functions of the gums and to prevent and treat periodontal diseases.

The main disadvantage of this technique is that, again contrary to the desirable effects of the apparatus and method of the present invention, the low and high frequencies in JP2001026529 cannot be applied over extended periods of time, and the apparatus only cleans the teeth and cannot be used for purposes of gum therapy.

Thus, known apparatuses in the field generate electromagnetic pulses of very low frequency, with intensities and amplitudes at times significantly less than those attributable to terrestrial magnetism. However, such electromagnetic fields all include a current component and exhibit harmonics by reason of same, whereby the effects of such apparatuses at the cellular level remain sub-optimal.

Earlier research on gum cell cultures by the applicant, the results of which were briefly in WO2012/093277, has shown that generating an extremely low frequency (ELF) magnetic field and subjecting organic cells to same provides a significant regenerating effect to the cells. The gum cell cultures were introduced into Petri containers and were subjected to an electromagnetic field of different pulsation and intensities, over different time periods, then the Petri containers were placed inside a Helmholtz-type assembly.

The apparatus used for generating the electromagnetic field in this research has two channels for generating electromagnetic impulses, each consisting of two oscillators with blocking, each of them generating an ELF frequency and operating alternatively, so that only one oscillator in a channel operates at a time according to a periodicity. The apparatus further includes a final circuit and an induction coil, which generate electromagnetic fields having the frequency of the oscillator of the selected channel, mixed with the frequency of a pilot oscillator and a selection circuit controlled by the pilot oscillator, which alternates the operation of the blocking oscillators, achieving the automatic change of the selectable frequency emitted by each channel by means of two control signals. In the above the above technique, disadvantageously the current does not remain constant and thus exhibits variations or harmonics within a same applied frequency, whereby the applied magnetic field is disturbed during its application to cellular tissue.

It is know that stem cells are undifferentiated biological cells that can differentiate into specialized cells and can divide (through mitosis) to produce more stem cells. They are found in multicellular organisms. In mammals, there are two broad types of stem cells: embryonic stem cells, which are isolated from the inner cell mass of blastocysts, and adult stem cells, which are found in various tissues. In adult organisms, stem cells and progenitor cells act as a repair system for the body, replenishing adult tissues. In a developing embryo, stem cells can differentiate into all the specialized cells-ectoderm, endoderm and mesoderm (see induced pluripotent stem cells)—but also maintain the normal turnover of regenerative organs, such as blood, skin, or intestinal tissues. There are three known accessible sources of autologous adult stem cells in humans:

Bone marrow, which requires extraction by harvesting, that is, drilling into bone (typically the femur or iliac crest), Adipose tissue (lipid cells), which requires extraction by liposuction, and Blood, which requires extraction through apheresis, wherein blood is drawn from the donor (similar to a blood donation), and passed through a machine that extracts the stem cells and returns other portions of the blood to the donor.

Stem cells can also be taken from umbilical cord blood just after birth. Of all stem cell types, autologous harvesting involves the least risk. By definition, autologous cells are obtained from one's own body, just as one may bank his or her own blood for elective surgical procedures.

Adult stem cells are frequently used in medical therapies, for example in bone marrow transplantation.

Stem cells can now be artificially grown and transformed (differentiated) into specialized cell types with characteristics consistent with cells of various tissues such as muscles or nerves. Embryonic cell lines and autologous embryonic stem cells generated through Somatic-cell nuclear transfer or dedifferentiation have also been proposed as promising candidates for future therapies.

In practice, stem cells are identified by whether they can regenerate tissue. For example, the defining test for bone marrow or hematopoietic stem cells (HSCs) is the ability to transplant the cells and save an individual without HSCs. This demonstrates that the cells can produce new blood cells over a long term. It should also be possible to isolate stem cells from the transplanted individual, which can themselves be transplanted into another individual without HSCs, demonstrating that the stem cell was able to self-renew.

Properties of stem cells can be illustrated in vitro, using methods such as clonogenic assays, in which single cells are assessed for their ability to differentiate and self-renew. Stem cells can also be isolated by their possession of a distinctive set of cell surface markers. However, in vitro culture conditions can alter the behavior of cells, making it unclear whether the cells will behave in a similar manner in vivo. There is considerable debate as to whether some proposed adult cell populations are truly stem cells.

The question is firstly whether to artificially increase the number of stem cells, both those in vitro and those that are found in various tissues in the body. A number of studies have documented similar effects of low frequency electromagnetic field on cell proliferation. The latest study in vivo (Komaki AI, Khalili A2, Salehi 12, Shahidi S2, Sarihi A2. Effects of exposure to an extremely low frequency electromagnetic field on hippocampal long-term potentiation in rat, 2014.03.041) highlight modulation of neuronal activity in Wistar rats, and the hypothesis is that synaptic plasticity is altered.

Experimental conditions (frequency and intensity) are however higher than in case of the system of the invention. Furthermore, a number of previous studies have shown the potential to influence neurogenesis by activating adult neuroprogenitor cells by electromagnetic field (Arias-Carrion, O., Verdugo-Diaz, L, Feria-Velasco, A., Milian-Aldaco, D., Gutierrez, A. A., Hernandez Cruz, A., Drucker-Colm, R., 2004. Neurogenesis in the subventricular zone following transcranial magnetic field stimulation and nigrostriatal lesions, *J. Neurosci. Res.* 78, 16-28).

It has been shown in vitro stimulation of neural stem cell differentiation, a phenomenon mediated upregulation of expression and channel activity Cavi (Piacentini et al., 2008). On the other hand, the passage of Ca ions through these channels influence the survival transcription of genes involved in cell proliferation and differentiation (Hardingham et al., 1998; Orrenius et al., 2003, West et al., 2001).

According to Ma et al. (2014), exposure to a 50 Hz field modulates the expression of mRNA for a number of molecules involved in cell proliferation.

Effects of exposure to EMF, which consist in modulation on protein phosphorylation cascades MAP/ERK has been demonstrated by Sheik et al. (2013) for endothelial cells. Effect on proliferation of dermal stem cells is demonstrated by Zhang et al. (2012); according to these authors, the effect depends on the frequency and duration of exposure, but are at higher frequencies, while they were also demonstrated such effects on proliferation and differentiation of mesenchymal stem cells (Vanoni et al., 2012). The technical problem to be solved thus consists in generating a constant medium value, non-deformed ELF magnetic field and subjecting stem cells to same for proliferation cellular.

SUMMARY OF THE INVENTION

According to an aspect of the present invention, there is therefore provided a system for proliferation of stem cells in cellular tissue in vivo or grown in vitro in vitro in repositories or cellular cultures laboratories, by local application of an extremely low frequency (ELF) magnetic field (MF) comprised by a generator for producing a sinusoidal extremely low frequency current signal, and at least a resonating medium connected to the generator, wherein, in a first embodiment:

the generator provides a constant sinusoidal extremely low frequency current signal which has a value $I_{RMs}=0.195$ A, one predetermined frequency chosen substantially from the range between 7.65 Hz and 7.75 Hz, and an induction of the said magnetic field substantially which has a value $B_{RMs}=0.75$ mT at a distance of 3 mm from the solenoid surface of the resonating medium, with harmonics substantially inferior to 0.2%, comprising:

a quartz oscillator which generates a rectangular signal, initially of a high precision frequency, which is successively divided through an first integrated circuit at the output of which a desired frequency between 3 and 30 Hz is obtained, and through a 8 order Butterworth filter-type integrated circuit by means of which the rectangular signal is converted into a sinusoidal signal, and a stage signal attenuator to provide only a current value to determine an induction in the range from 0.25 mT-2 mT, each stage of the attenuator leading to an increase by 0.25 mT of the induction of the magnetic field obtained at an emitter of the resonating medium;

and wherein at least one resonance medium operably connected to the generator, comprises at least a coil having number of loops wounded about an emitter made of magnetic material, the resonance medium being subjected to said current signal which has the one predetermined optimal frequency chosen substantially from the range between 7.65 Hz and 7.75 Hz, and, the induction of the said magnetic field substantially has a value $B_{RMs}$ 0.75 mT at a distance of 3 mm from the solenoid surface of the resonating medium, with harmonics substantially inferior to 0.2%;

said magnetic field being applied in a transversal direction to a localized region of the stem cells.

According to another of the present invention, the first integrated circuit comprises a synchronous counter, a first and second asynchronous counter, a plurality of resistors and a plurality of switches, the first integrated circuit being configured to switch one or more resistors of the plurality thereof by one or more switches of the plurality thereof, and divide the frequency by N=1 to 256 with the synchronous counter and divide the frequency by 2 <8> with the first asynchronous counter as a function of the switched resistors.

According to another aspect of the present invention, the multi-stage signal attenuator comprises 8 stages and wherein each stage is adapted to increase the induction of the magnetic field of the resonance medium by 0.25 mT.

According to another aspect of the present invention, the generator is further configured to adjust the electromagnetic current signal according to an anatomic known depth, being the desired depth of the organic cells within the relative region.

According to another aspect of the present invention, the depth is in the range of 1 millimeter to 100 millimeters, preferably 3 mm.

According to another aspect of the present invention, the support member is made of a paramagnetic material.

According to another aspect of the present invention, the emitter comprises two tine portions projecting from a base portion defining a U-shape and made integrally of magnetic material, and wherein the at least one coil member is wound about the base portion.

According to an aspect of the present invention, a system is provided for proliferation of stem cells in cellular tissue in vivo or grown in vitro in repositories or cellular cultures laboratories, by local application of an extremely low frequency (ELF) magnetic field (MF) comprised by a generator for producing a sinusoidal extremely low frequency current signal, and at least a resonating medium connected to the generator, wherein, in a second embodiment:

the generator provides a single value sinusoidal extremely low frequency current signal and one predetermined frequency chosen substantially from the range between 7.65 Hz and 7.75 Hz, so the induction of the said magnetic field substantially which has a value $B_{RMs}=0.75$ mT at desired depth from the solenoid surface of the resonating medium, with harmonics substantially inferior to 0.2%, comprising:
  a Direct Digital Synthesizer adapted to directly generate the sinusoidal signal, with harmonics substantially inferior to 0.2% and which generates a precise sinusoidal current signal within a range of 7.65 Hz and 7.75 Hz managed by a processor;
  an amplification unit of constant current to ensure at the level of emitter an induction potentially up to 3 mT, controlled by the processor,
  and wherein
  the output from the amplification unit is applied to relevant terminals of the generator which are operably connected with a coil member (30) of the resonating medium and;
  wherein
  at least one resonance medium operably connected to the generator, comprises at least a coil having number of loops wounded about an emitter made of magnetic material, the resonance medium being subjected to the current signal which has the one predetermined optimal frequency chosen substantially from the range between 7.65 Hz and 7.75 Hz, and the induction of the magnetic field substantially has a value $B_{RMs}=0.75$ mT at a distance of 3 mm from the solenoid surface (20a) of the resonating medium (20), with harmonics substantially inferior to 0.2%; and
  the magnetic field being applied in a transversal direction to a localized region of the stem cells.

According to another aspect of the present invention, the support member is chosen from the group comprising at least a belt, a mask, a helmet, a dressing, a pillow, and a mattress with a plurality of resonance medium connected to the generator and secured in place in order to ensure, at a desired depth, uniformity of the signal, and to avoid any interference or disturbance of the electromagnetic fields proved by measurements with a teslameter.

According to an aspect of the present invention, a method is provided for proliferation of stem cells grown in vitro in repositories or cellular cultures laboratories, by local application of an extremely low frequency (ELF) magnetic field (MF), comprising the steps of:
  sampling stem cells;
  subjecting stem cells to a first magnetic field, resulted by setting the generator of the system to generate a first sinusoidal electric current signal having a first frequency chosen substantially from the range between 7.65 Hz and 7.75 Hz;
  subjecting stem cells from the same region to at least a second magnetic field, resulted by setting the generator of the system to generate a second sinusoidal electric current signal having a second frequency chosen substantially from the range between 7.65 Hz and 7.75 Hz, wherein the first and second frequencies are different;
  determining the rate of cellular growth according to each of the frequencies to which the organic cells were subjected to;
  selecting the optimum frequency providing the highest rate of cellular growth, preferably at 7.69 Hz;
  adjusting the generator of the system to emit the electric current signal having the optimum frequency only, and
  submitting cellular cultures or cellular tissues grown in vitro to the respective optimum frequency two hours per day over a minimum of 5 exposures.

According to an aspect of the present invention, the system of the invention is used for regenerating cellular tissue composed of cells having keratin therein, preferably for hair growth, to reduce wrinkles, skin creases, stretch marks and skin inelasticity.

According to an aspect of the present invention, the system of the invention is used for vegetals.

BRIEF DESCRIPTION OF THE FIGURES

For a better understanding of the invention and to show how the same may be carried into effect, there will now be described by way of example only, specific embodiments, methods and processes according to the present invention with reference to the accompanying drawings in which.

SPECIFIC DESCRIPTION

There will now be described by way of example a specific mode contemplated by the inventors. In the following description numerous specific details are set forth in order to provide a thorough understanding. It will be apparent however, to one skilled in the art, that the present invention may be practiced without limitation to these specific details. In other instances, well known methods and structures have not been described in detail so as to not unnecessarily obscure the description.

The invention relates to a system for proliferation of stem cells which use an apparatus for the local application of an extremely low frequency (ELF) magnetic field to a localized region of organic cellular tissue, whether human, animal or vegetal.

Figure 1:
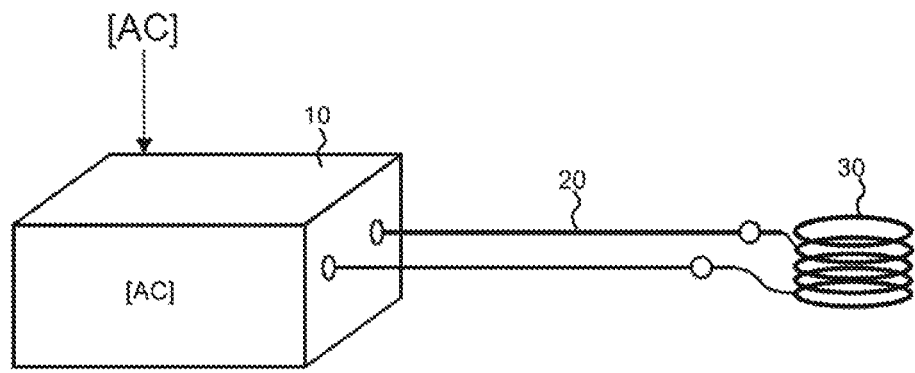
FIG. 1 is a block diagram of a generator apparatus and resonance medium for the local application of an extremely low frequency ELF magnetic field according to the invention.

With reference to FIG. 1, at its simplest, the apparatus comprises a generator 10 including circuitry for producing a constant and sinusoidal extremely low frequency current signal, and a resonating medium 20 operably connected to the generator for the localized application of a correspondingly constant extremely low frequency electromagnetic field produced from the generator signal. A defining characteristic of the apparatus is that the constant extremely low frequency electromagnetic field produced by the resonating medium 20 from the constant and sinusoidal extremely low frequency current signal supplied by the generator 10 has no voltage and, as such, is considered to be a magnetic field in the region of cellular tissue subjected to it. With the apparatus, the frequency of the ELF field is fixed, and its intensity at the level of the target region is substantially 0.75 mT, thus its intensity may be somewhat higher at the level of the emitter, potentially up to 3 mT when the region is intracorporal.

Figure 2A:
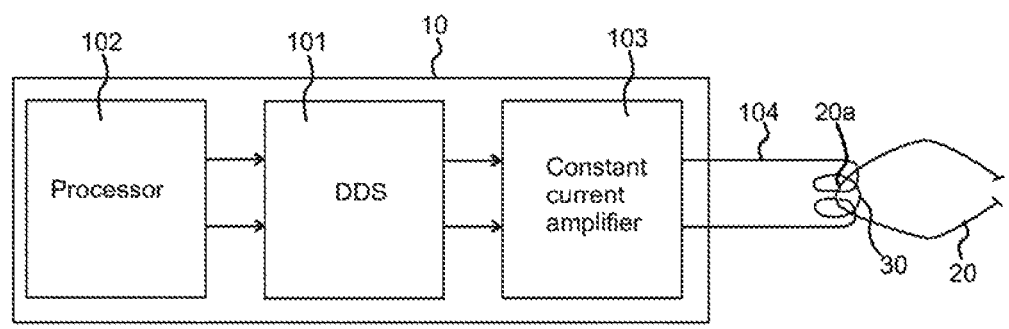
FIG. 2A is a block diagram of a first embodiment of a circuit of the apparatus of FIG. 1 for producing the ELF magnetic field according to the invention.

With reference to FIG. 2A, in order to obtain a single sinusoidal extremely low frequency current signal, a first embodiment of the circuitry of the generator 10 contains a Direct Digital Synthesizer (DDS) 101 adapted to directly generate the sinusoidal signal, with harmonics substantially inferior to 0.2% and which does not require any processing of the signal with the components described with reference to FIG. 2C hereafter. The DDS 101 generates a precise sinusoidal signal within a range of 2 to 50 Hz which, in the example, is fixed to 7.692 Hz. The signal generated by the DDS 101 has high precision and stability managed by a processor 102. The sinusoidal signal generated by the DDS 101 is input to an amplification unit 103 of constant current adjustable within a range of 1 to 600 mA which, in the example, is fixed to 195 mA. Both the frequency and the current are continuously controlled by the processor 102. The output from the amplification unit 103 is applied to relevant terminals of the generator 10 which are operably connected 104 with a coil member 30 of the resonating medium 20. A circuit diagram corresponding to an embodiment of the circuitry of the generator 10 shown in FIG. 2A is shown by way of a non-limiting example in FIG. 2B.

Figure 2B:
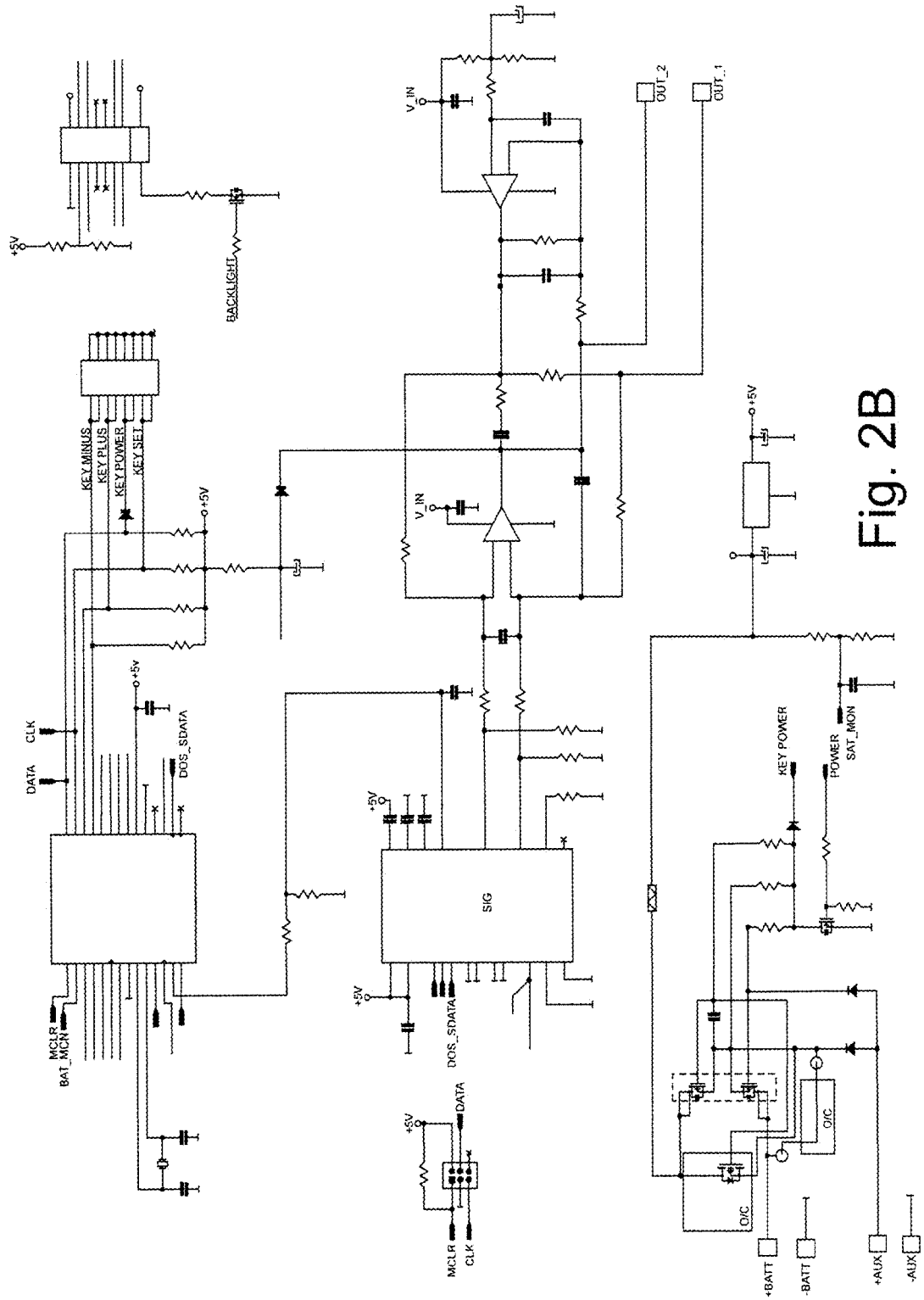
FIG. 2B is a circuit diagram of the embodiment of FIG. 2A for producing the ELF magnetic field according to the invention.
Figure 2C:
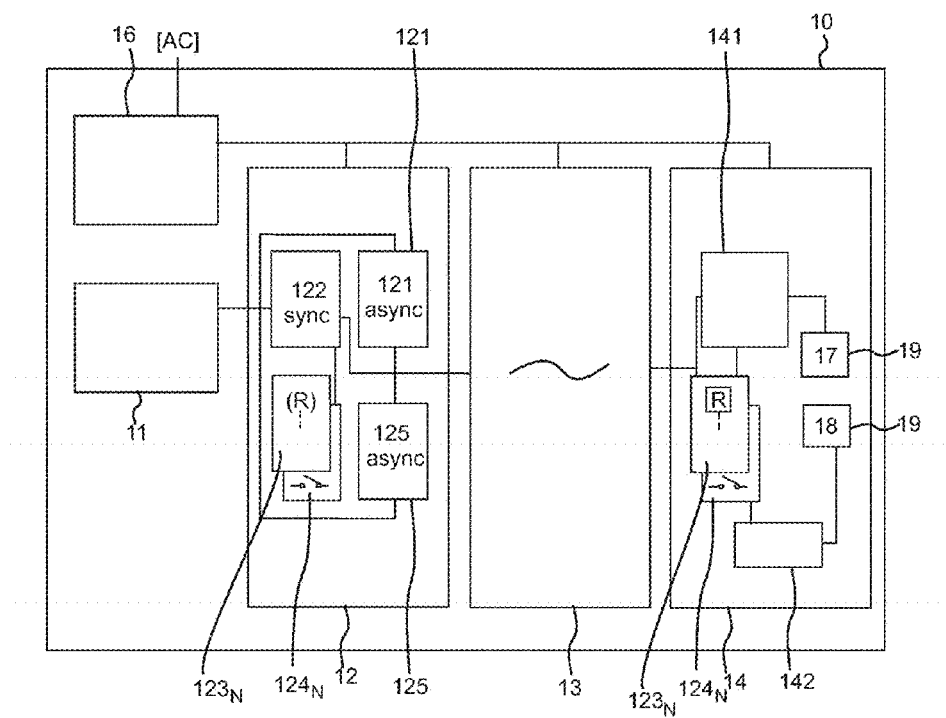
FIG. 2C is a block diagram of a further embodiment of a circuit of the apparatus of FIG. 1 for producing the ELF magnetic field according to the invention.
Figure 3:
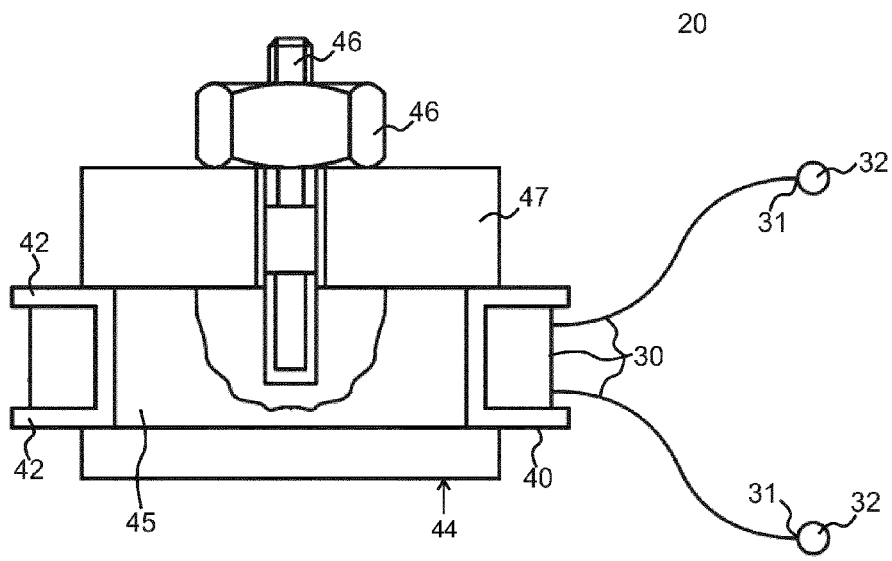
FIG. 3 is a lateral view of a first embodiment of a resonance medium for the local application of an extremely low frequency ELF magnetic field, in the form of a coil member mounted to an emitter.
Figure 4:
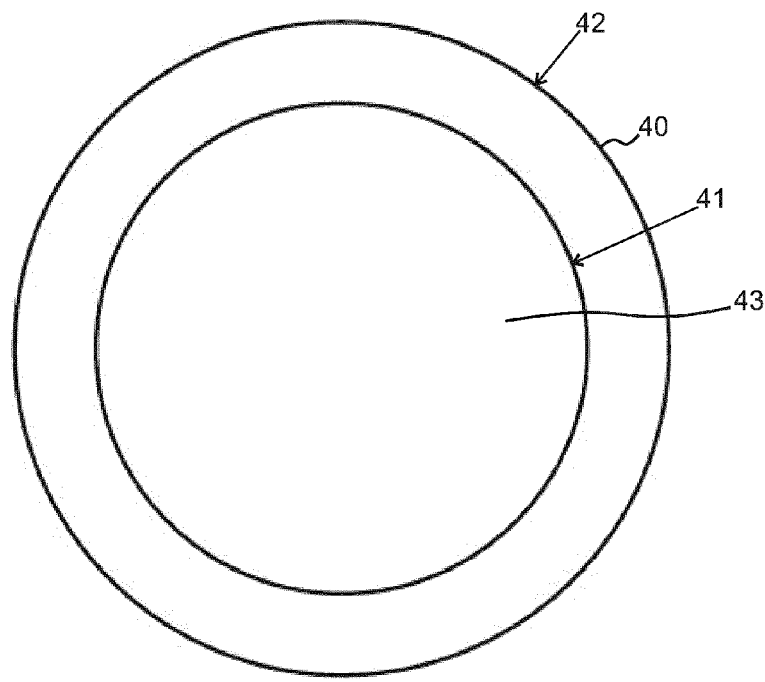
FIG. 4 is a top view of the coil member of FIG. 3.

With reference to FIG. 2C, a further embodiment of the circuitry of the generator 10 contains a quartz oscillator 11 which generates a rectangular signal, initially of a high precision frequency known to be 3.6864 MHz, which is successively divided through an integrated circuit 12, at the output of which a desired frequency between 3 and 30 Hz is obtained. The circuitry further includes an order Butterworth filter-type integrated circuit 13 by means of which the rectangular signal, consisting of an infinite series of rectangular signals, is converted into a sinusoidal signal, i.e. a sinusoid of a predetermined certain frequency is selected; an eight-stage signal attenuator 14 for supplying a current in the range from 0.25 mT-2 mT, each stage of the attenuator 14 leading to an increase by 0.25 mT of the induction of the magnetic field obtained between some polar parts 15 of the resonating medium 20, and a constant current source 16 for maintaining the current constant.

The integrated circuit 12, at the output of which the desired frequency ranging from 3 to 30 Hz is obtained, consists of an asynchronous counter 121 at which the frequency is divided by 24; a synchronous counter 122 at which the frequency will be divided by N=1 to 256, as a function of the switching of one or more of a plurality of resistors $123_i$-$123_8$ introduced into the circuit by a plurality of electronic switches $124_i$-$124_{10}$; and another asynchronous counter 125 at which the frequency will be divided by 28. Thus the asynchronous counter 121, the synchronous counter 122, the asynchronous counter 125, the resistors $123_i$-$123_8$ and the electronic switches $124_i$-$124_{10}$ constitute the integrated dividing circuit 12.

The signal output by the quartz oscillator 11 is applied to the input of the asynchronous counter 121 at which the frequency is divided by 24, then to the input of the synchronous counter 122 at which the frequency is divided by N=1 to 256, depending on the value of the switched resistors $123_i$-$123_8$. The signal is then applied to the input of the further asynchronous counter 125 at which the frequency is divided by 28. At the end of the dividing stage, consisting of the two asynchronous counters 121, 125 and the synchronous counter 122, the desired frequency ranging from 3 to 30 Hz is obtained.

The sinusoidal signal is then applied to the eight-stage signal attenuator 14, in order to supply a current signal in the range of 0.25 mT-2 mT. Each stage of this attenuator 14 leads to an increase by 0.25 mT of the induction of the magnetic field generated by the resonating medium 20.

The eight-stage signal attenuator 14 consists of at least first and second integrated circuits 141 and 142, a plurality of resistors $143_i$-$143_8$ and a plurality of electronic switches $144_i$-$144_8$, configured so that when the switch 144a is closed, the signal at the output of the first integrated circuit 141 is applied to the input of the second integrated circuit 142 directly, the maximum value of the voltage and the current corresponding to the maximum value of 2 mT of the magnetic induction, and if the switch 1441 is closed, the signal at the output of the first integrated circuit 141 is applied to the input of the second integrated circuit 142 via the resistors $143_i$-$143_8$, the minimum value of the voltage and current corresponding to the minimum value of 0.25 mT of the magnetic induction.

The source of constant current 16 makes available voltage levels necessary for the operation of the first and second integrated circuits 141, 142 and at least first and second bipolar transistors 17, 18 providing corresponding voltage signals and, in order to maintain the current constant throughout the apparatus of the invention, thus in the circuit consisting of the components 11, 12, 13, and 14 comprised in the generator 10, the resonating medium 20 and any polar parts thereof and the connection between the generator and the resonating medium, the constant current source 16 is configured to adequately vary the voltage at terminals, so that the current in the load circuit remains constant.

The constant current source 16 makes available the voltage levels required for the operation of the integrated circuits 141 and 142 of the bipolar transistors 17, 18. By offering corresponding voltage signals, the constant current source stabilizes the current through the load, thereby avoiding any variation of the signal in the resonating medium 20 and, by transition, maintains the magnetic field emitted by the resonating medium and any polar parts thereof constant, according to the following function:

$B=f(H)$ or $U=1(1)$ linear.

In the above, B represents the induction, H represents the shape of the current signal at the output, the function translating the fact that the current shape at the output H observes the shape of the applied voltage, namely of the induction B. This is advantageous because it allows a non-deformed magnetic field to be obtained between any polar parts 15 of the resonating medium 20.

It is notoriously difficult to directly calculate the field of a circular coil outside its axis, and even the H intensity within the axis is hard to define, as the magnetic potential $\varphi_m$ should first be determined then, from its derivative, the distance from the coil would be obtained as:

$$Hx = -\frac{\partial \varphi_m}{\partial_x}$$

The Biot-Savart law provides an appropriate means to calculate an electromagnetic field value at a point M on the solenoid axis, when a distance d>>r such as:

$$r = R_2 + \frac{R_1 - R_2}{2}.$$

However, the result of this approach is not very accurate since, in the context of the present disclosure, the distance d is not higher than r. Accordingly, the result of this approach has been selected as a starting point, to be further corrected with effective field measurements.

The calculation starts from an initial hypothesis, that the resonating medium 20 has a circular surface of 10|11 cm$^2$ and the low frequency sinusoid field induction has a value $B_{RMs}$ of 0.750 mT at a distance of 3 mm from the solenoid surface (20a) of the resonating medium 20. In this situation, the physical dimensions of the resonating medium 20 are:

$R1=2$ cm, $R2=1.4$ cm and the average radius of the resonating medium 20 is:

$r=(R1-R2)/2+R2=1.7$ cm

Applying Biot-Savart provides the following dependency relation:

$Hx=f(N,I)$ and respectively $Bx=f(\mu,N,I)$ wherein Hx can be expressed as:

$$Hx = \frac{I}{2r}\sin^3\alpha \text{ where } \sin\alpha = \frac{r}{\sqrt{r^2 + d^2}}$$

and wherein Bx, which shall be the imposed measurement $B_{RMs}=0.750$ mT, can be expressed at point M along the axis as:

$$Bx = \frac{\mu_0}{4\pi} \cdot \frac{Ir^2}{2(r^2 + d^2)^{3/2}}.$$

The above remains valid in the case of an alternative sinusoidal current, for instance, with a frequency f=7.692 Hz in the present example. Hx and Bx decrease rapidly when x is increasing. By introducing the sinusoidal measurement, expressed as:

$i=I \max \sin \omega t$,

Bx can now be expressed as:

$$Bx = 0.21 \frac{\mu_0}{4\pi} N \cdot i = 0.21 \frac{\mu_0}{4\pi} NI\sqrt{2} \sin(48.3t).$$

Thus, the following dependency relation is obtained for this embodiment:

$$Bx = f(\mu, N, I),$$

wherein: µ=magnetic permeability of the core; N=number of loops; and I=current within the coil.

In use, any of the embodiments of FIGS. 2A to 2C may be used singularly to apply the ELF field onto a region of stem cellular tissue of a subject, substantially as described herein. For best results, however, the embodiment of FIG. 2C may first be used in laboratory conditions to determine the most appropriate frequency for the subject, and thus, the most appropriate frequency at which to emit the ELF field. Then, the embodiment of FIG. 2A or 2B may be adjusted to emit at the determined frequency. Accordingly, in this embodiment, organic cells sampled from the region are subjected to a first constant sinusoidal, non-harmonic current signal output by the embodiment of FIG. 2C, having a first frequency of substantially between 7.5 Hz and 7.9 Hz, for instance 7.682 Hz, and an electromagnetic radiation of substantially 0.75 mT. Further organic cells sampled from the region are then subjected to one or more further constant sinusoidal non-harmonic current signals, each with a different frequency within the above interval, for instance a second signal with a frequency of 7.692 Hz. A rate of cellular growth is determined for each such signal, and the frequency providing the highest rate of cellular growth, for instance the second frequency of 7.692 Hz, is selected as the most appropriate frequency. The embodiment of FIG. 2A or 2B is then adjusted to emit at that selected frequency only.

With reference to FIGS. 3 to 6, a first embodiment of the resonating medium 20 comprises a coil member 30 having 251 loops, the current value $i_{RMs}$ is 0.195 A. Physical dimensions of the coils may vary depending on the application. The coil member 30 is made of CuEm 0.31 and each extremity 31 thereof is terminated with a respective connector 32, for operable and releasable attachment to relevant terminals 19 of the eight-stage signal attenuator 14 of the generator 10.

The resonating medium 20 further comprises a circular modular support medium 40 having a substantially H-shaped section, which consists of a central cylindrical section 41 delimited by shouldering sections 42 at each extremity, and a though-aperture 43 co-axial with the central cylindrical section 41. The coil member 30 is wound about the external surface 41 of the central cylindrical section of emitter 44 between the shouldering sections 42. The modular support member 40 houses a emitter 44 with a first surface 45 facing the cellular tissue onto which the ELF magnetic field is emitted. The emitter 44 may be made of any magnetic material, such as medical grade steel or, in a preferred embodiment, permalloy.

The emitter 44 has a substantially cylindrical shape with an external diameter dimensioned to achieve a sliding fit into the though-aperture 43, and a threaded aperture co-axial with the though-aperture 43 and extending from a second surface parallel to and opposed to the first surface 45, substantially at the figurative rear of the circular modular support medium 40. The emitter 44 is secured in place with a fastener 46 engaging both its threaded aperture and a spacer member 47 abutting the shouldering section 42 opposed to the first surface 45 and having a larger diameter than the though-aperture 43 of the circular modular support medium 40.

Figure 5:
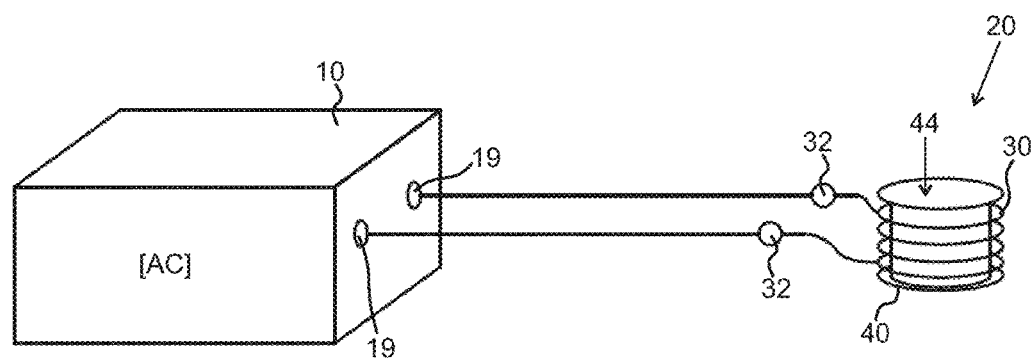
FIG. 5 shows the resonance medium of FIGS. 3 and 4 operably connected with the generator apparatus of FIGS. 1 and 2.
Figure 6:
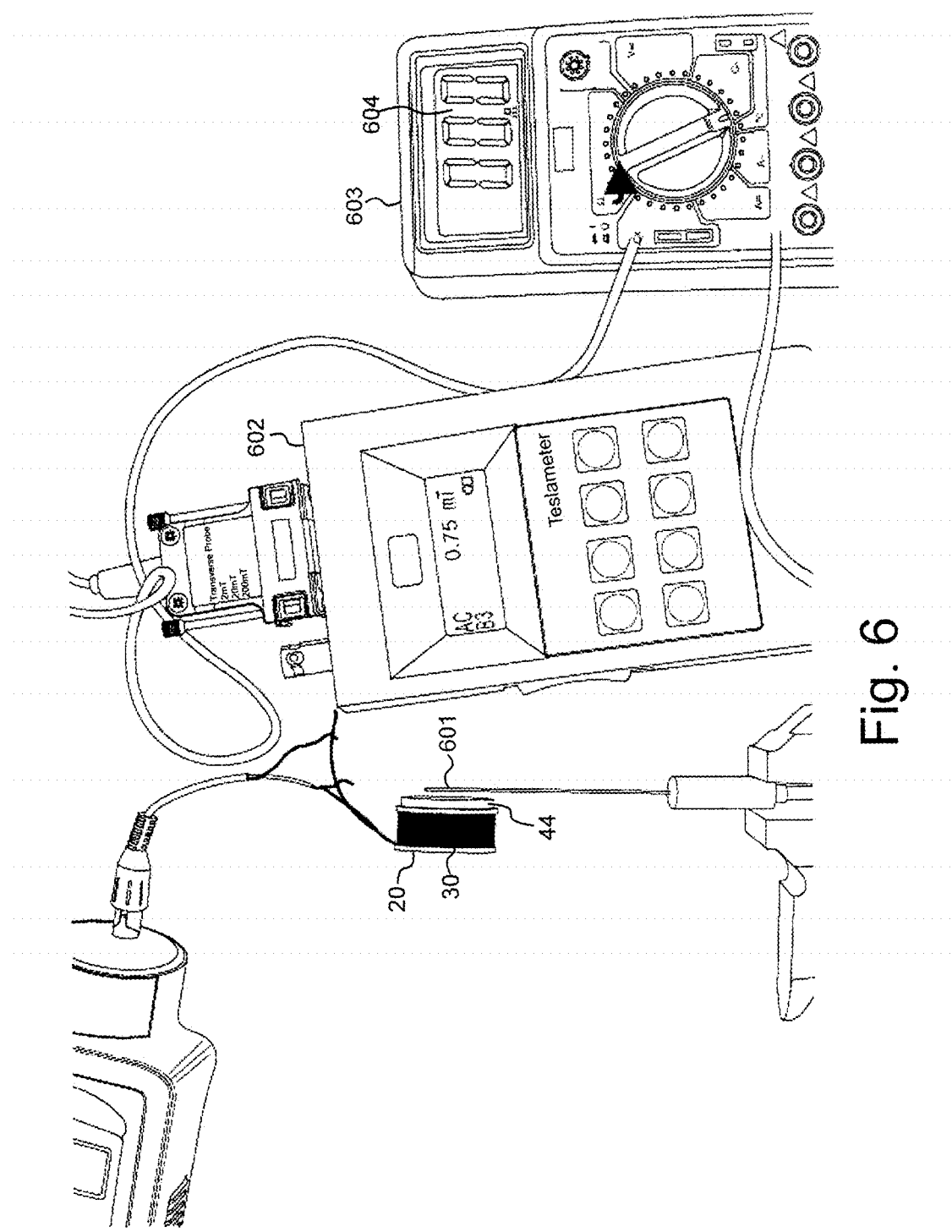
FIG. 6 shows measurements of the electromagnetic field emitted by the coil member of FIG. 5 by an adjacent probe interfaced with a teslameter and a voltmeter.

With reference to FIG. 5, in use, the coil member 30 is supplied with the constant and undisturbed ELF electromagnetic current signal by the generator of FIG. 2A, 2B or 2C, which causes the emitter 44 to emit a correspondingly constant and undisturbed ELF electromagnetic field. With reference to FIG. 6 in particular, which shows measurements of the electromagnetic field emitted by the coil member 30 coupled with the emitter 44 by an adjacent probe 601 interfaced with a teslameter 602 and a voltmeter 603, an important characteristic of the electromagnetic field emitted is that it does not contain detectable electric components using conventional voltmeter, s 603, and is therefore considered to be a purely magnetic field at the level of the cellular region to which it is applied.

Figure 7:
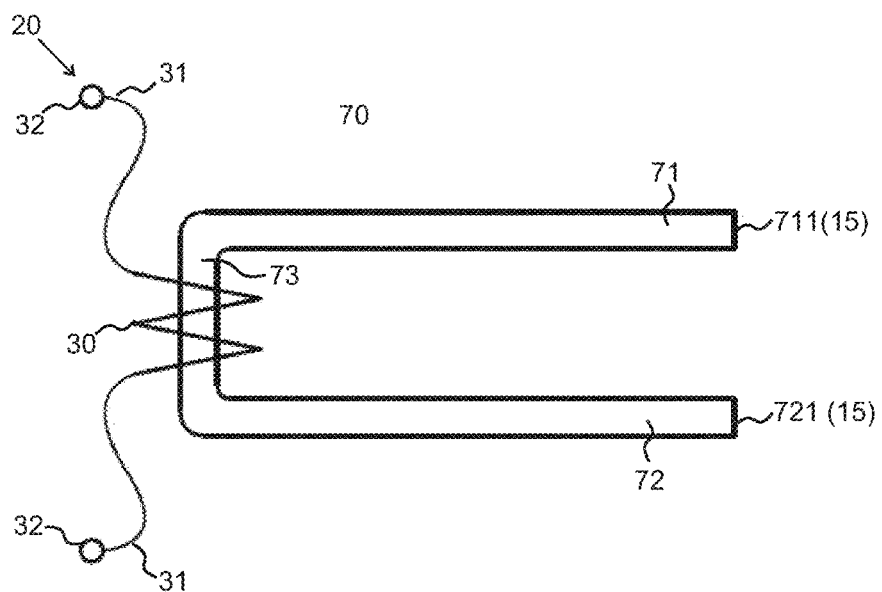
FIG. 7 is a top view of a second embodiment of a resonance medium for the local application of the ELF magnetic field, in the form of a coil member wound about a fork-like emitter and particularly adapted for use in the buccal cavity.
Figure 17:
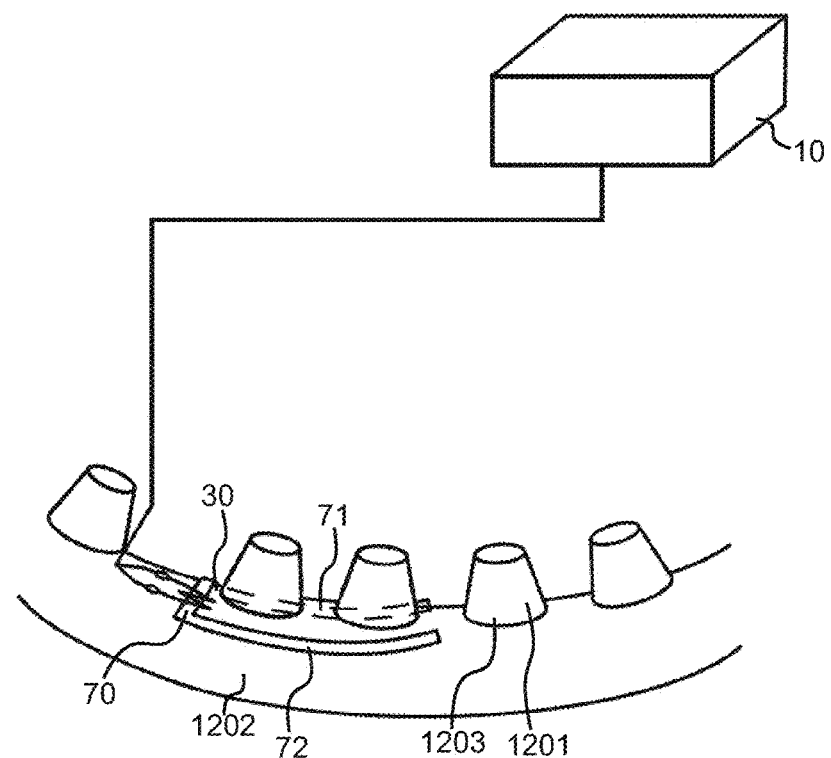
FIG. 17 shows the resonance medium of FIGS. 7 to 12 in use within a buccal cavity.

With reference now to FIGS. 7 and 17, a further embodiment of the resonating medium 20 again comprises a coil member 30 having 251 loops, the current value $I_{RMs}$ is 0.19 A. Physical dimensions of the coils may vary depending on the application. The coil member 30 is again made of CuEm 0.31 and each extremity 31 thereof is terminated with a respective connector 32, for operable and releasable attachment to relevant terminals (not shown in these Figures) of the eight-stage signal attenuator 14 of the generator 10.

In this embodiment, the resonating medium 20 further comprises a coil 30 wound on a substantially U-shaped emitter 70 defined by two tine portions 71, 72 projecting from a base portion 73 and made integrally from a bar of permalloy, which is a nickel-iron alloy with a very high magnetic permeability at high values of the induction and, consequently, a very low hysteresis, so that the saturation risk of the material is as low as possible, and the non-deformed character of the sinusoidal magnetic field is maintained. This embodiment is deemed particularly useful for buccal application of the ELF field, typically to a region 1201 of the jaw, of the gum 1202 or of a tooth 1203, with the tines 71, 72 disposed either side of the said region 1201 and the ELF field emitted there between.

Each of the tine portions 71, 72 and the base portion 73 is substantially rectilinear with a cylindrical cross-section. The two tine portions 71, 72 have substantially the same dimensions and extend substantially parallel to one another from the base portion 73, with which they respectively form a right angle. The free extremities 711, 721 of the tine portions 71, 72 constitute polar parts 15, between which the region of cellular tissue to be subjected to the ELF is located in use.

An alternative embodiment considers a threaded aperture implemented transversally and co-axially within each tine portion 71, 72 and extending from the free, at least partially beveled extremity 711, 721 thereof, and the adjunction of a cylindrical screw engaged in each such aperture, each screw acting as one polar part for the application of the magnetic field onto the desired jaw portion, gum or tooth. In this embodiment, the coil member 30 is wound about the external surface of the base portion 73, substantially between its extremities from which the tine portions 71, 72 respectively project.

The configuration of the resonating medium 20 in the embodiment of FIGS. 7 to 12 requires reconsideration of the above function, as follows and based on an example electromagnetic field of, substantially, $B_{RMs}$=0.750 mT at a frequency of 7.692 Hz. In this example, the law of circuit magnetism is applied such that:

$$\oint_1 \overline{Hds} = H_f I_f + H_\delta I_\delta = NI$$

wherein N=number of loops, and I=current within the coil.

The length of iron circuit If is given by:

$$l_f = \left(\frac{b-a}{2} + a\right)2\pi - l\delta = 18 \text{ cm}$$

$$l\delta = 2 \text{ cm.}$$

With replacement in the above, the following is obtained:

$$18H_f + 2H\delta = NI. \quad (2)$$

The magnetic flux is known to be constant along the flux tube, such that:

$$B_f \cdot A = B_\delta \cdot A_\delta \text{ and } B_\delta = \mu_0 H_\delta \quad (3)$$

Figure 19:
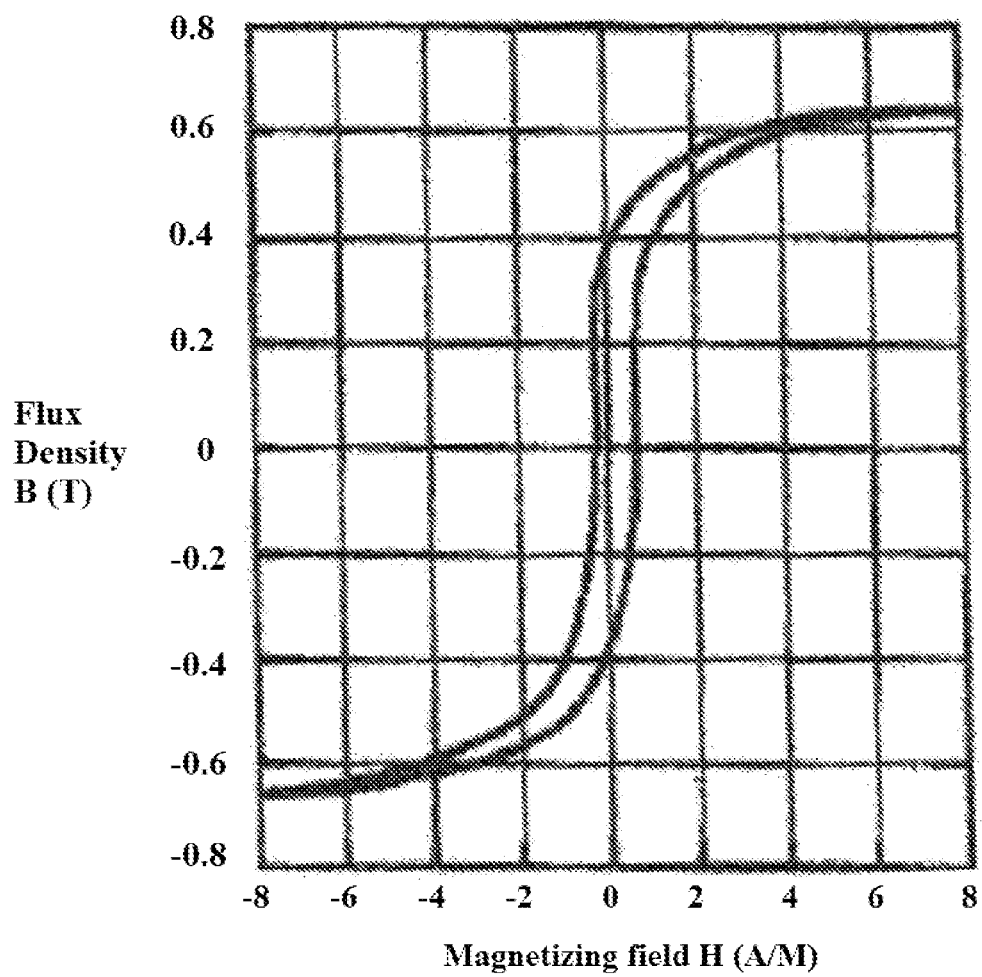
FIG. 19 shows diagram of the current in coil and correspondent flux density.

The problem is solved by a method of successive approximation: in order to calculate the current in the coil, for which a certain induction should be achieved in permalloy, the solution is direct. $B_f$ and $B_\delta$ obtained at (3) are plotted relative to μ, whereby the respective intensities of the field $H_f$ and $H_\delta$ are obtained as shown in FIG. 19.

The current in the coil 30 is then obtained from (2). In the example, the following results were obtained:

$$i = i_o \sin \omega t = i_o \sin(48.3t)$$

$$I_{RMS} = 0.19 \text{ A}$$

N=381 sp; CuEm 0.2

It will be readily understood by the skilled person that many variations may be readily devised to improve the ergonomic properties of the resonating medium 20, without departing from the scope of the present disclosure. With reference to the embodiment of FIG. 7, for instance, an alternative embodiment considers a mechanism to articulate at least one tine portion 71, 72 relative to the base portion 73, thus located substantially at the junction therebetween, in order to vary the distance between the tine portions 71, 72 and the polar parts 15 constituted by their respective extremities 711, 721.

Figure 8:
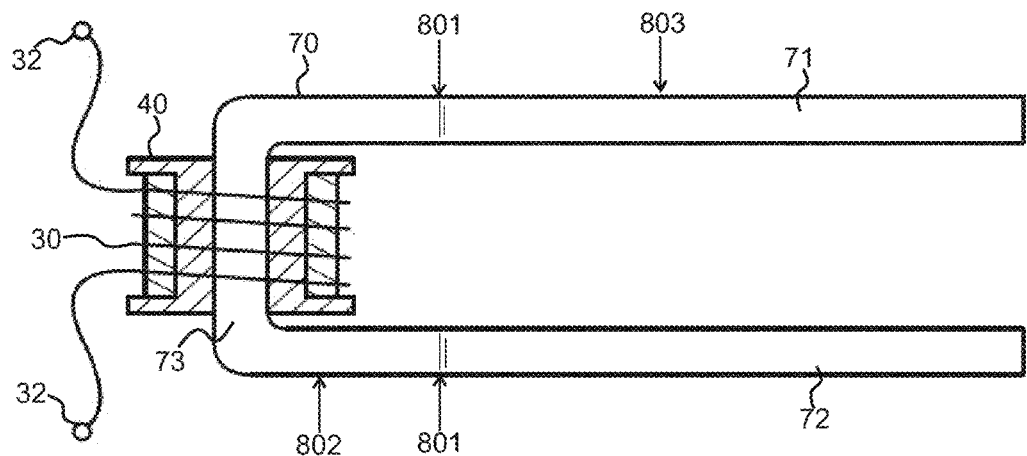
FIG. 8 is a top view of a third embodiment of a resonance medium for the local application of the ELF magnetic field, based on the second embodiment of FIG. 7.
Figure 9:
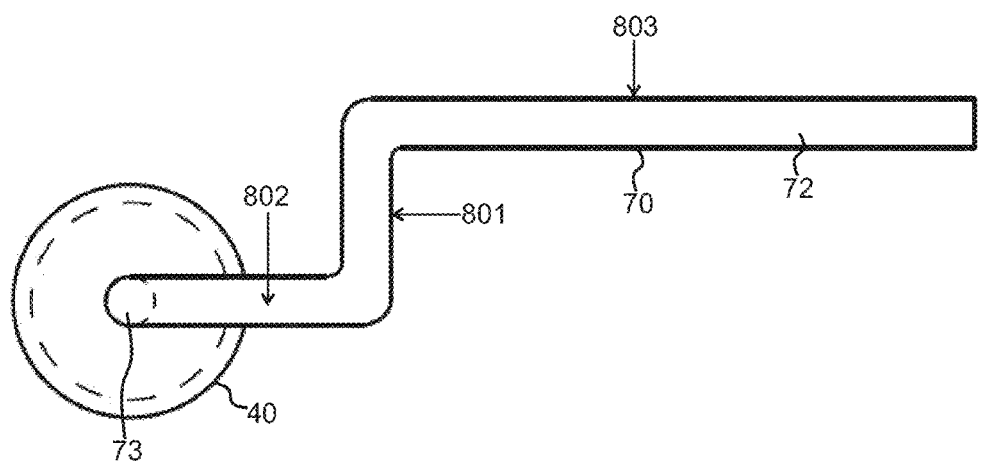
FIG. 9 is a lateral view of the third embodiment of FIG. 8.

If desired, at least part of the base portion 73 of the resonating medium may be housed in a plastic material in the shape of a handle, as shown in FIGS. 8 and 9, for facilitating its handling.

A constant sinusoidal electric current of extremely low frequency is thus obtained from the generator 10 of FIGS. 1 and 2, and is applied to the resonance medium 20 to obtain an extremely low frequency magnetic field that is applied to a localized region of cellular tissue.

Figure 10:
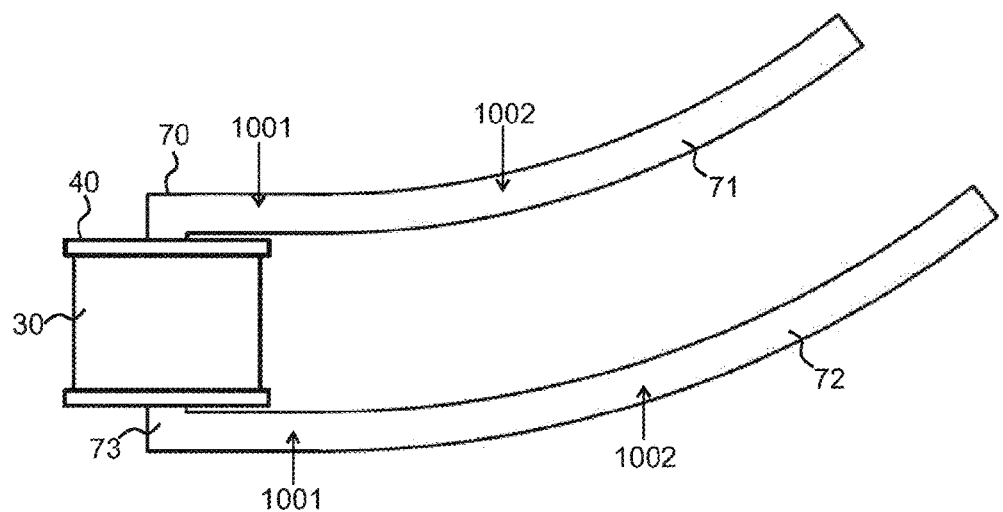
FIG. 10 shows a fourth embodiment of a resonance medium for the local application of the ELF magnetic field, again based on the second embodiment of FIG. 7.

FIGS. 8, 9 and 10 present further alternative embodiments of the substantially U-shaped member 70 of the emitter. With reference to FIGS. 8 and 9, the base portion 73 and two tine portions 71, 72 may retain the configuration substantially as previously described with reference to FIG. 7. However, in this embodiment, each of the two tine portions 71, 72 comprises a dog leg defined by a short section 801 of the tine portion 71, 72 forming a right angle between a first part 802 of the tine 71, 72 nearest the base portion 73 and a second part 803 of the tine 71, 72 furthest the base portion 73, whereby the dog leg is located substantially intermediate the base portion 73 and the polar extremity 15. This embodiment is particularly useful for an oral application over prolonged periods of time, as the dog leg allows the parallel tine portions 71, 72 to abut a resting surface outside the buccal cavity, for instance the lip of a person.

With reference to FIG. 10, the rectilinear base portion 73 may still form a right angle relative to the respective sections 1001 of the two tine portions 71, 72 most adjacent the base portion 73, however in this embodiment each tine portion 71, 72 comprises a curvilinear section 1002 extending from its section 1001 most adjacent the base portion 73. In this embodiment, both tine portions 71, 72 maintain parallelism along their length until their respective polar extremities, thus defining a curve relative to and extending away from the base portion 73. This embodiment is particularly useful for an oral application over prolonged periods of time, as the curve allows the base portion to abut upon a resting surface outside the buccal cavity, for instance the cheek of a person. The respective embodiments of FIGS. 8 to 10 may be used iteratively or, with reference to the example embodiments described hereafter which use several resonating media 20 at the same time, in conjunction with one another, depending on the region and the number thereof to be treated in a buccal cavity.

Figure 11:
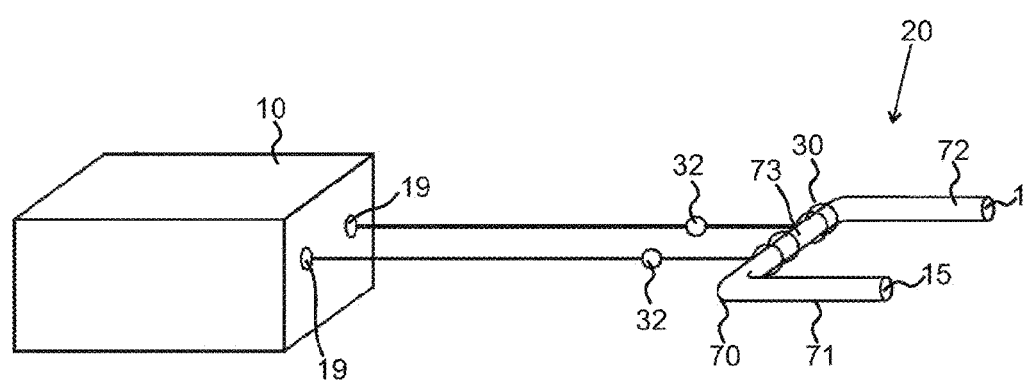
FIG. 11 shows the resonance medium of FIG. 7 operably connected with the generator apparatus of FIGS. 1 and 2.
Figure 12:
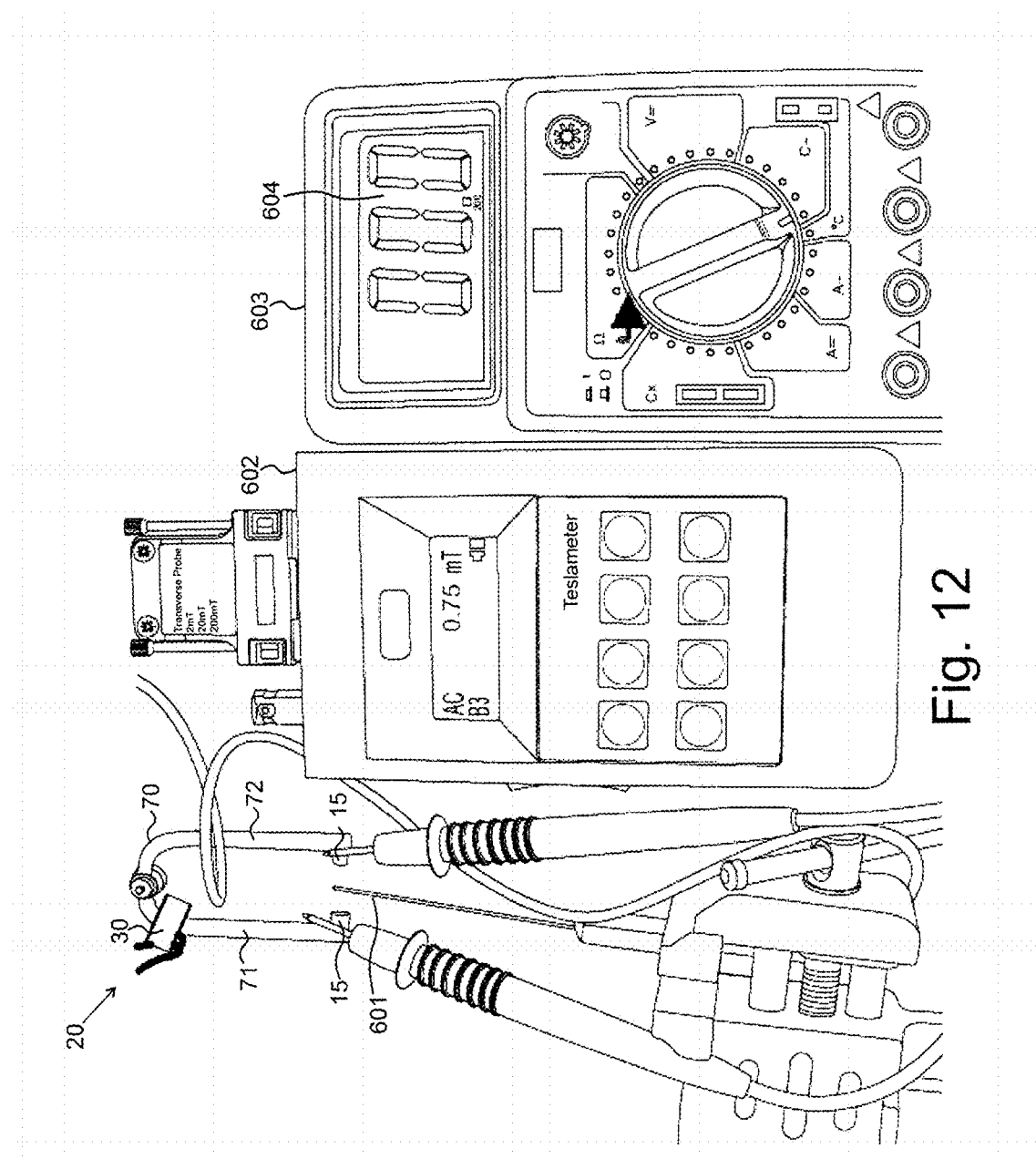
FIG. 12 shows measurements of the electromagnetic field emitted by the fork-like emitter of FIG. 11 by an adjacent probe interfaced with a teslameter and a voltmeter.

With reference to FIG. 11, in use, the coil member 30 is again supplied with the constant and undisturbed ELF current signal by the eight-stage signal attenuator 14 of the generator 10 which causes the U-shaped, or fork-shaped, emitter 70 to emit a correspondingly constant and undisturbed ELF electromagnetic field. With reference to FIG. 12 in particular, an important characteristic of the electromagnetic field emitted is that, again, it does not contain a detectable current component, and is therefore considered to be a purely magnetic field at the level of the region to which it is applied.

In tests of the apparatus according to the invention, optimum results were obtained when cell cultures were subjected to an electromagnetic field having an intensity of 0.75 mT to 0.8 mT maximum, and a constant frequency fixed at 7.692 Hz.

The optimum duration of exposure was determined as 2 hours per day over a minimum of 5 exposures. The tests showed that, with such parameters, a proliferation by 25 to 27% of the number of cells was obtained in all cultures.

Use of the apparatus according to the invention as shown in FIG. 11 has been tested under express confidentiality, in respect of cellular tissue in the buccal cavity, and details and results of the tests are described hereafter. All subjects experiencing gum issues were characterized by a cellular deficit in the gum region causing the issue, and all subjects treated with the apparatus of the invention have shown a regenerative effect of the gum issue over a shorter period of time than expected. The fork embodiment of the resonating medium 20 was used since a Helmholtz coil assembly cannot be introduced into a subject's buccal cavity.

For purposes of isolating and cultivating primary keratinocytes, oral mucosa was obtained from patients undergoing tooth extraction. Tissues were rinsed and cut into smaller pieces and subjected to enzymatic dissociation in Dispase II and Collagenase for 24 hours at 4° C. After treatment, the epidermal sheet was removed from the connective tissue. To obtain viable single keratinocyte cells, the epithelial sheets were treated with trypsin for 30 min at 37° C. The cells were re-suspended in EpiLife® medium supplemented with calcium, growth supplements and antibiotics. The cells were plated in 35 mm diameter dishes pre-coated with human collagen type IV.

For purposes of separating oral keratinocyte stem cells, the cells will be incubated with mouse monoclonal integrin α6β4. After removing excess antibodies, the cells were further reacted with goat anti-mouse IgG MicroBeads (Miltenyi Biotec Inc.) then the cell suspension was loaded into a column placed in the magnetic field of a MACS® Separator (Miltenyi Biotec Inc.). The unlabeled cells were processed through the column and represented the α6β4 negative (α6β4 neg) fraction, whereas magnetically-labeled cells, representing the α6β4 positive (α6β4 pos) cell fraction, were retained in the column. After 2 to 3 days from the first separation, the α6β4 pos cell fraction was magnetically labeled with CD71 MicroBeads and subjected to the same procedure of magnetic cell sorting. The magnetically labeled CD71 positive (CD71 pos) cells were retained in the column, whereas the unlabeled CD71 negative (CD71 neg) cells were processed through the column. After the two magnetic separations, the α6β4 pos CD71 neg fraction represented the oral keratinocyte stem cells fraction.

The oral keratinocyte stem cells were then stimulated with the apparatus of the invention for 7 days, i.e., subjected to a constant non-deformed ELF magnetic field of 7.692 Hz and 0.75 mT, and cellular development was assessed at 3 and 7 days.

Figure 20:
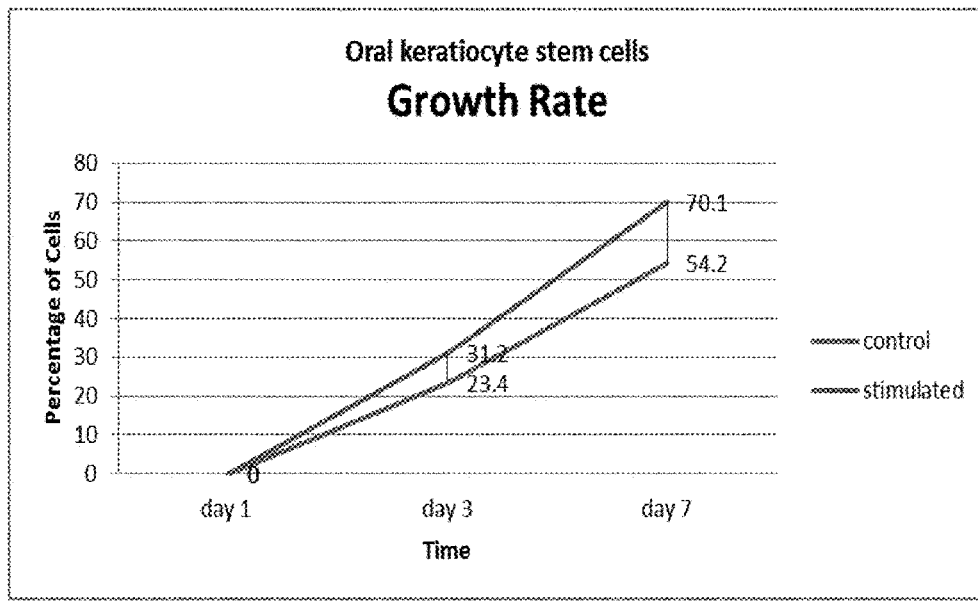
FIG. 20 shows graph of the results of the stimulation.

National Institute "Victor Babes", Bucharest, Romania was a series of tests conducted for the system and method according to the invention on the effects of stimulating mesenchymal stem cell proliferation or differentiation into adipocytes, chondrocytes and osteocytes. The result of these tests is shown in FIG. 20.

For mesenchymal stem cell proliferation, the proliferation of mesenchymal stem cells was performed in passage no. 3 in 12-well plates, utiliand proiferare environment completely.

Tests were performed in the conditions (standard control culture) and expunele conitii in the system according to the invention, the settings –6.93 Hz, 7.69 Hz B-, C-, and D 8.46 HZ-23 Hz.

Cultures were exposed to the system for 2 hours a day, starting 24 hours after the onset of the culture for 3 days (at 24, 48 and 72 hours). In 48 hours, serum replacement with fresh medium was performed.

At 20 and 96 hours of cultivars, the medium was replaced with medium to which was added 0.1% MTS reagent, was incubated for 3 hours, then the supernatant was collected and measured at 490 nm optical activity (MTS test). After a 20 hour test (initial test), the medium was changed with commonly MSC growth medium, replacing medium supplemented with MTS.

There have been indications in original cells at 20 hours and then at 96 hours, so normalized indices were calculated for each culture separately, thus avoiding variations caused by uneven cell load.

Results from three independent experiments for the three variants and controls are summarized in Table 1.

TABLE 1

|  | Nenormalized | Normalized (96-20 h) | P |
|---|---|---|---|
| Control | 100 | 100 | |
| A | 102 | 104 | <0.1 |
| B | 118 | 123 | <0.05 |
| C | 106 | 109 | <0.05 |

Figure 21:
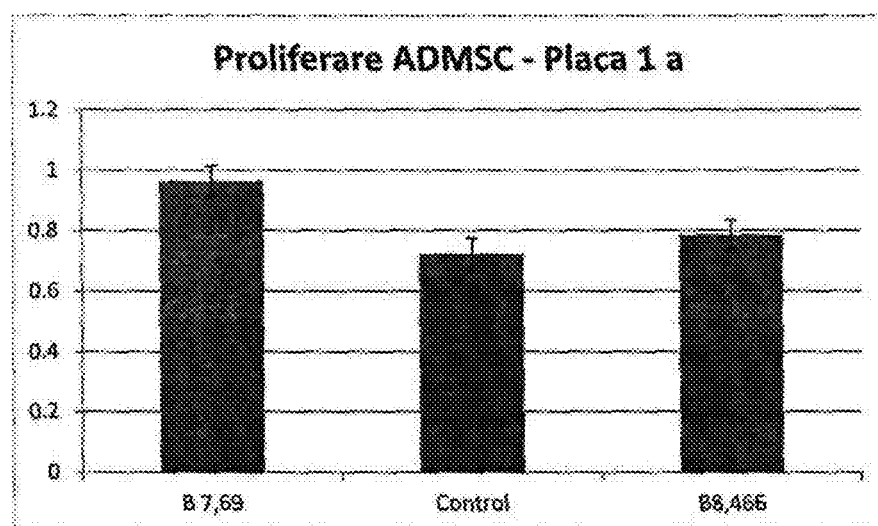
FIG. 21 shows The graph of growth of stem cells tested.
Figure 22:
FIG. 22 shows culture ADSC, 48 hours, unexposed (20×)
Figure 23:
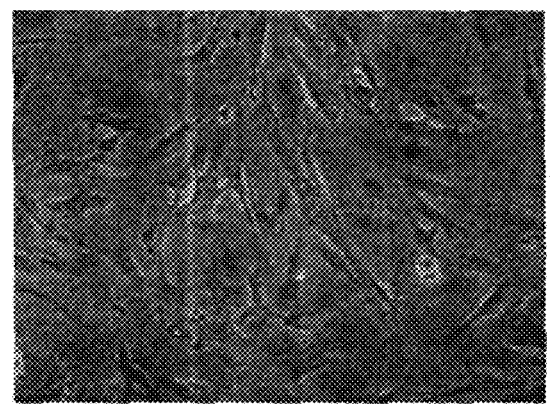
FIG. 23 shows culture ADSC, 48 hours, coil 7.69 Hz. Ob. (20×)
Figure 24:
FIG. 24 shows culture ADSC, 48 hours. 7.69 Hz. (Ob. 10×).

In accordance with the above data, there is a stimulation of stem cell proliferation in setting B (medium frequency) by a factor of approximately 23% (p<0.05). Similarly, but with a smaller coefficient statistically significant and observed in higher frequency, was 9%, (p<0.05), while the lowest frequency values were not statistically significant. The graph of increase in stem cell analysis is shown in FIG. 21. In accordance with the above data, there is a stimulation of proliferation of stem cells for setting B (medium frequency) by a factor of approximately 23% (p<0.05). Similarly, but with a smaller coefficient statistically significant and observed in higher frequency, was 9%, (p<0.05), while the lowest frequency values were not statistically significant. In FIGS. 22 to 24 are shown images of ADSC cultures at 48 hours. Objective 20× (1 unexposed) was compared to culture exposed to 7.69 Hz frequency opitima (2 Ob., 3×20, ob. 10×). One can see the typical stem cell morphology (morphology of fibroblast cells) that is conserved in the exposed cells, and the difference in cell density (higher in cells exposed).2

For adipocyte differentiation, differentiation of mesenchymal stem cells was performed in No passage. 4 in 12-well plates, using the environment differentiation and maintaining complete adipocyte differentiation.

Tests were performed under standard conditions (culture control) and conditions i.e., exposure at system of the invention, to the settings A, B, and C.

Cultures were exposed to the device ED for 2 hours per day, from 24 hours after installation in the culture for 3 days (at 24, 48 and 72 hours). At 48 hours serum replacement was done with fresh medium. At 20, 96 hours to the cultivars, and at 18 days to the cultivars, the medium was replaced with medium of the same type, supplemented with 0.1% MTS reagent, was incubated for 3 hours, and then the supernatant was collected and optical activity was measured at 490 nm (MTS test). After a 20 hour test (first test) was done to changes in the differentiation inducing medium, supplemented media in the place of MTS and subsequently maintaining medium differentiation.

There were initial cell indices (at 20 hours) from, and then at 96 hours from and 18 days, so the normalized indices for each culture was determined separately, thus avoiding variations caused by uneven cell load.

Results from three independent experiments for the three variants and for controls are summarized in Table 2.

TABLE 2

| Differentiation indices | | | | | |
|---|---|---|---|---|---|
|  | Nenormalized | Normalized (96-120 h) | P | Final (18* days) | |
| Control | 100 | 100 | | | |
| A | 101 | 102 | <0.1 | 101 | <0.1 |
| B | 108 | 112 | <0.05 | 106 | <0.05 |
| C | 103 | 105 | <0.1 | 103 | <0.05 |
| D | 98 | 100 | NA | 100 | NA |

If frequency d is observed as reduced cell number compared with the control, which demonstrates that 3 harmonic of the main frequency has the negative effects and therefore harmonics should be reduced to the maximum, according to the invention, so as to be reduced to a level below 0.2%. In accordance with the above data, there is a stimulation of stem cell differentiation in the adipocytes setting B (medium frequency) by a factor of approximately 12% (p<0, 05). Similarly, but with a smaller coefficient statistically significant, it was observed in higher frequency (5%, p<0.05) while the lowest frequency values were not statistically significant. Highest frequency is (D) but does not show the same effects. The same trend was observed at the final time, even if the intensity of the effect was slightly lower. Apparently, however, the dominant effect is the phenomenon associated with cell proliferation, at the stage in which the fraction of stem cells is still high, then enter a relative plateau-surpassing increased number of cells, with the roll-out of differentiation. Specific staining for lipids was positive in all the cultures.

For chondrocyte differentiation, chondrocyte differentiation of mesenchymal stem cells was performed in passage no. 4 in the 96-well plates, using the environment of chondrocyte differentiation. Tests were performed under standard conditions (culture control) and exposure conditions in the system of the invention, to the settings A, B, and C.

Cultures were exposed to the device ED for 2 hours a day, starting 24 hours after installation in the culture for 3 days (at 24, 48 from and 72 hours).

In 48 hours, serum replacement proceeded with fresh medium.

Thereafter, exposure was made every 3 days for two hours. A final determination (MTS test) was made at the end of the experiment (day 18).

At 20 hours 96 cultivars and 18 days of cultivation, the medium was replaced with medium of the same type, supplemented with 0.1% MTS reagent and was incubated for 3 hours, then the supernatant was collected and measured activity optic 490 nm (MTS assay). After 20 hour test (first test) was done by changing the medium to the normal for chondrocyte differentiation medium, supplemented with MTS environment instead. There have been indications original cell (20 hours) from and then at 96 hours from and 18 days, as yet normalized index for each culture separately, thereby avoiding variations arising from uneven cell load.

TABLE 3

| Results from three independent | Unnormalized | Normalized (96-20 h) | P | Final (18 days) | |
|---|---|---|---|---|---|
| Control | 100 | 100 | | | |
| A | 101 | 101 | | 100 | |
| B | 106 | 105 | <0.05 | 105 | <0.05 |
| C | 103 | 102 | | 102 | |

According to the above data, there is a stimulation of the differentiation of chondrocytes to the set B (medium frequency) by a factor of about 6% (p<0, 05), to the 96 hour by 5% in the end. Other frequency resulted in modest statistically insignificant stimulation.

Specific staining for Ca was positive in all cultures.

For differentiation osteocytes, differentiation of mesenchymal stem cells was performed in passage no. 4 in the 12-well plates, using the environment differentiating osteocytes.

Tests were performed under standard conditions (culture control) and system conditions reveals invention settings A, B, and C.

Cultures were exposed to the device ED for 2 hours a day, starting 24 hours after installation in the culture for 3 days (at 24, 48 from and 72 hours). At 48 hours, proceed to replace serum with the fresh medium. Then, exposure was made every 3 days for two hours. A final determination (MTS test) was performed at the end of the experiment (day 18). At 20, 96 from and 18 hours cultivars days of culture, the medium was replaced with medium of the same type, supplemented with 0.1% MTS reagent, was incubated for 3 hours, then the supernatant was collected from and measured to the optical activity 490 nm (MTS assay). After 20 hour test (first test) was done by changing the medium to the normal for the osteocyte differentiation medium, supplemented with MTS environment instead.

There were initial cell indices (at 20 hours) from and then at 96 hours and 18 days so still normalized indices for each culture separately, thus avoiding variations caused by uneven cell load.

TABLE 4

| Results from three independent | Unnormalized | Normalized (96-20 h) | P | Final (18 days) | |
|---|---|---|---|---|---|
| Control | 100 | 100 | | | |
| A | 102 | 102 | | 102 | |
| B | 109 | 111 | <0.05 | 110 | <0.05 |
| C | 103 | 104 | | 104 | |

According to the above data, there is a stimulation of the differentiation of osteocytes to the set B (medium frequency) by a factor of about 11% (p<0, 05), to the 96 hour, and 11% at the end. Setting C also stimulates proliferation, 3, and 4% in the final as statistically significant. Specific staining with Alizarin red Ca was positive in the all cultures that were sampled to be analyzed to identify any disturbances in the signal transduction.

The composition of the cells of gum tissue includes keratin, which proteic substance is found in the composition of many types of cells. Accordingly, skilled readers will readily appreciate that the apparatus can also be employed for treating cellular tissues which include keratin in their composition, such as hair and skin, with a view to increasing the number of regenerative cells and eliminating wrinkles or for other affections of the skin, and for improving the integration of implants, whether dental or otherwise, by improving the receiving bed before the implanting and hastening the regeneration after the implanting.

The apparatus of the invention accordingly lends itself to a very wide variety of cosmetic and therapeutic uses and alternative embodiments consider varying the depth of the region subjected to the optimum electromagnetic field relative to an external surface, such as the skin or jaw bone of a person by way of example. At its simplest, the depth of optimum emission may be varied by adding or subtracting loops from the coil 30.

Figure 13:
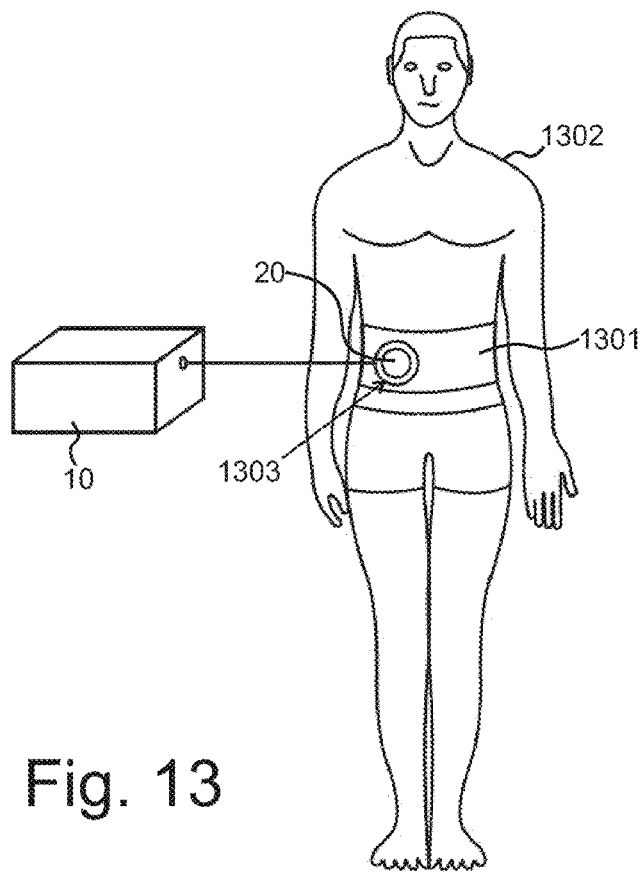
FIG. 13 shows the resonance medium of FIGS. 3 to 6 mounted to a first support medium in the form of a dressing.

Thus, a first example of use of the apparatus according to the invention shown in FIG. 5 is shown in FIG. 13, which illustrates a resonating medium 20 embodied as a coil 30 wound about an emitter 44 interfaced with a generator 10, sewn or otherwise secured in place on a flexible dressing or band 1301 located about the abdomen of a subject 1302 over a localized region 1303 to be treated. This embodiment may be used to subject an internal organ, for instance the liver or a kidney, to the ELF EM field of the invention. In this example, the liver regeneration will occur as a result of progenitor cells which exist in the liver, proliferation under the action of the ELF EM field.

Figure 14:
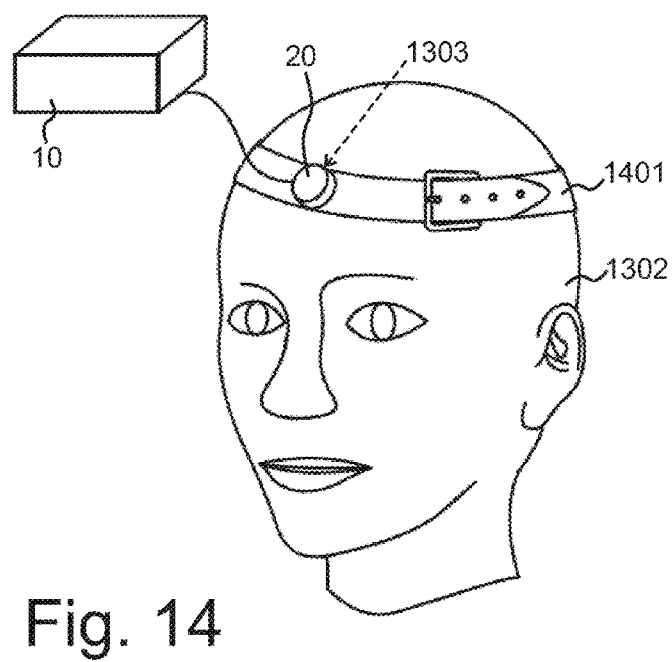
FIG. 14 shows the resonance medium of FIGS. 3 to 6 mounted to a second support medium in the form of support of an adjustable belt.

A second example of use of the apparatus according to the invention shown in FIG. 5 is shown in FIG. 14, which again illustrates a resonating medium 20 embodied as a coil 30 wound about a emitter 44 interfaced with a generator 10. In this embodiment, sewn or otherwise secured in place on an adjustable belt 1401 located about the head of a subject 1302 over a localized region 1303 to be treated is a plurality of adjustable belts forming a helmet. This embodiment may be used to subject the epidermis of the subject 1302 to the ELF EM field of the invention, in order to improve its elasticity and reduce wrinkles, creases and the like. Alternatively, the same embodiment may be used to remedy localized hair loss.

Figure 15:
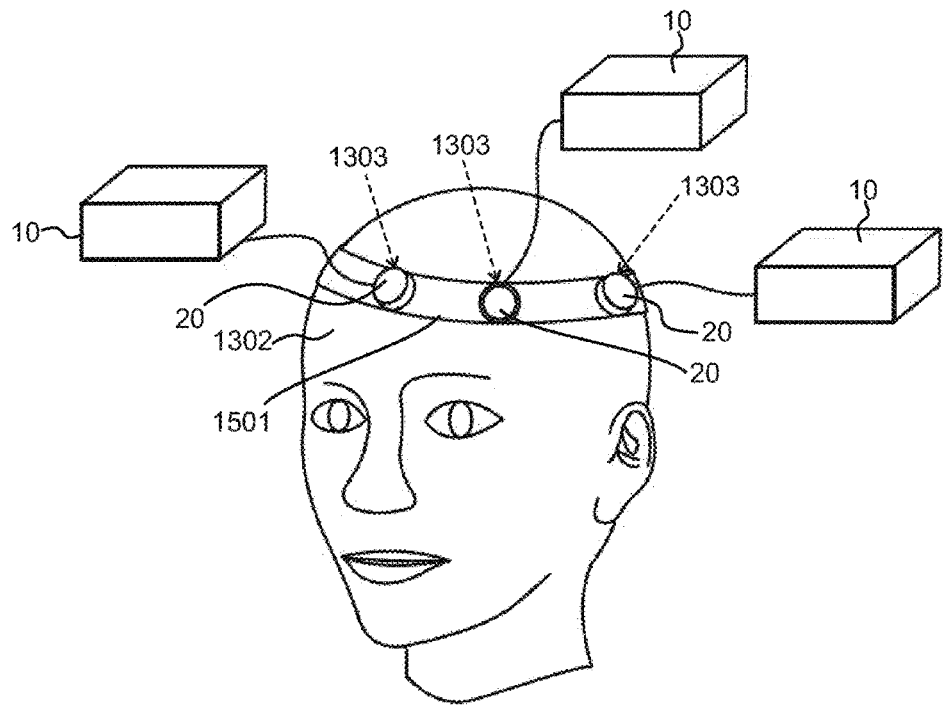
FIG. 15 shows a plurality of resonance media of FIGS. 3 to 6 connected to respective generator apparatuses mounted to the second support medium of FIG. 14.

An alternative of this embodiment is shown in FIG. 15, which considers the simultaneous use of a plurality of resonating media 20 embodiment sewn or otherwise secured in place on an adjustable belt 1501, each interfaced with a respective generator 10 to ensure uniformity of the signal at each resonating medium 20 and to avoid any interference or disturbance of the respective ELF EM fields within their respective regions 1303.

An alternative of this embodiment is represented by a plurality of resonating media 20 connected in serial with a single generator.

This embodiment may be used for treating skin wrinkles, skin creases such as stretch marks, cellulitis and the like, or to remedy hair loss, over a wider area of a subject.

Figure 16:
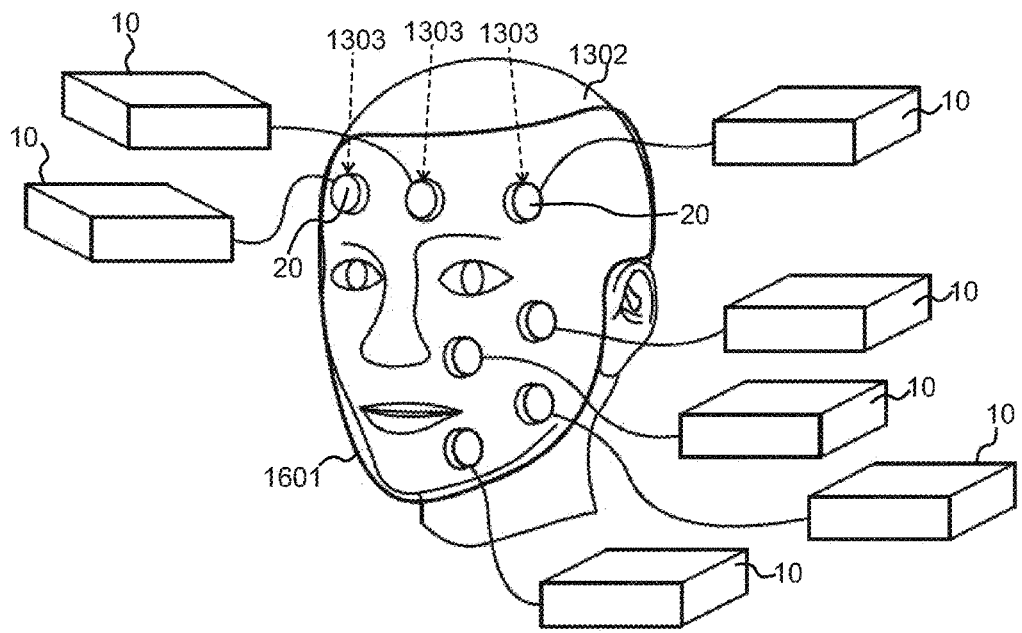
FIG. 16 shows a plurality of resonance media of FIGS. 3 to 6 connected 10 to respective generator apparatuses mounted to a third support medium in the form of a mask.

It will be readily understood by the skilled person that very many alternative embodiments are possible based on the above-described principles, without departing from the scope of the present disclosure. In particular, with reference to the principle of simultaneous use of several resonating media 20 as described above and shown in FIG. 15, an alternative of this embodiment is shown in FIG. 16, which again considers the simultaneous use of a plurality of resonating media 20 embodiment sewn or otherwise secured in place on a face mask 1601, each again interfaced with a respective generator 10, wherein this embodiment may again be used for treating wrinkles, creases and the like. As an alternative, a helmet may be used for application about the head other than to the face. Alternative embodiments consider the use of a plurality of resonating media 20 fixedly sewn or otherwise secured to a support medium which is typically used for extended periods of time, in particular a mattress or a pillow. Such embodiments are considered particularly advantageous for preventing decubitus ulcers that are known to occur when a subject rests for prolonged periods of time after a procedure.

Figure 18:
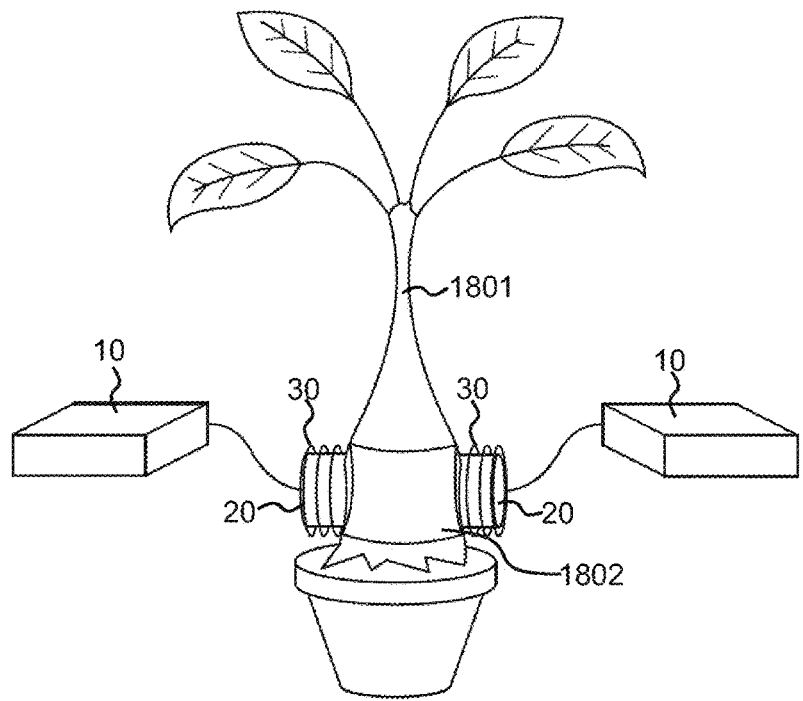
FIG. 18 shows a plurality of resonance media of FIGS. 3 to 6 connected to respective generator apparatuses in use with vegetal cellular tissue.

Further, use of the apparatus according to the invention is not limited to human or animal cells, but has been shown to provide a beneficial effect upon vegetal cells. Accordingly, a further example of use of the apparatus according to the invention is shown in FIG. 18, which illustrates a pair of resonating media 20 each embodied as a coil 30 wound about a emitter 44 on a support medium 40 interfaced with a generator 10, in this embodiment sewn or otherwise secured in place on an adjustable belt 1802 located about the trunk of a plant 1801.

Further beneficial effects arising from the application of an extremely low frequency magnetic field may be expected in the following cases: chronic and acute rheumatism, migraines, joint pains, arthritis, osteoporosis, deficient blood circulation, sexual dysfunctions, insomnia, neurosis, concentration incapacity, meteorological discomfort, breathing problems, metabolism disorders etc. It can be said that the application of an extremely low frequency ELF magnetic field onto a cellular tissue causes the following main effects: anti-inflammatory effect; neo-antigenic effect, by increasing the proliferation of endothelial cells and their tubulization and the increased production of fibroblasts; re-epithelization effect by stimulating the formation of collagen; improved fertility by increasing the proliferation of spermatogenic cells.

Accordingly, the system of the invention may be used for proliferation cellular tissues grown in vitro, such as epidermis, cornea, liver endothelium, ligaments and membranes, besides others. In particular, as has been suggested by the experiment described above, repositories of harvested cells may use the method and system of the invention for economically proliferation stem cells and progenitor cells.

In the specification the terms "comprise, comprises, comprised and comprising" or any variation thereof and the terms include, includes, included and including" or any variation thereof are considered to be totally interchangeable and they should all be afforded the widest possible interpretation and reciprocally. The invention is not limited to the embodiments hereinbefore described but may be varied in both construction and detail.

The invention claimed is:

1. A system for proliferation of stem cells, in cellular tissue in vivo or grown in vitro in repositories or cellular cultures laboratories, by local application of an extremely low frequency magnetic field, said system comprising a generator for producing a constant sinusoidal extremely low frequency current signal, and at least one resonating medium connected to the generator, wherein:

the generator comprises:
a quartz oscillator which generates a rectangular signal, initially of a high precision frequency,
a first integrated circuit which successively divides the rectangular signal to output a desired frequency between 3 and 30 Hz,
an 8 order Butterworth filter integrated circuit which converts the divided rectangular signal into a sinusoidal signal, and
a multi-stage attenuator which provides a current value to produce an induction of the magnetic field in a range from 0.25 mT-2 mT at an emitter of the at least one resonating medium, each stage of the attenuator leading to an increase of 0.25 mT of the induction of the magnetic field;

the at least one resonance medium comprising the emitter and at least one coil member having a number of loops wound about the emitter, the emitter being made of magnetic material, the at least one resonance medium being subjected to said sinusoidal extremely low frequency current signal produced by the generator;

the sinusoidal extremely low frequency current signal having a value of $I_{RMs}$=0.195 A and a predetermined frequency chosen from a range between 7.65 Hz and 7.75 Hz with harmonics inferior to 0.2%, and an induction of the magnetic field having a value $B_{RMs}$=0.75 mT at a distance of 3 mm from a solenoid surface of the at least one resonating medium; and said magnetic field being applied in a transversal direction to a localized region of the stem cells.

2. The system according to claim 1, wherein the first integrated circuit comprises a synchronous counter, a first and second asynchronous counter, a plurality of resistors and a plurality of switches, the first integrated circuit being configured to switch one or more resistors of the plurality of resistors by one or more switches of the plurality of switches, and divide the rectangular signal frequency by 24 with the first asynchronous counter, divide the rectangular signal frequency by N=1 to 256 with the synchronous counter and divide the rectangular signal frequency by 28 with the second asynchronous counter as a function of the switched resistors.

3. The system according to claim 1, wherein the multi-stage signal attenuator comprises 8 stages.

4. The system according to claim 1, wherein the generator is further configured to adjust the constant, sinusoidal extremely low frequency current signal according to an anatomic known depth of the stem cells within the localized region.

5. The system according to claim 4, wherein the depth is in a range of 1 millimeter to 100 millimeters.

6. The system according to claim 5, wherein the depth is 3 mm.

7. The system according to claim 1, further comprising a support member made of a paramagnetic material.

8. The system according to claim 1, wherein the emitter comprises two tine portions projecting from a base portion defining a U-shape and made of magnetic material, and wherein the at least one coil member is wound about the base portion.

9. The system according to claim 1, further comprising a support member chosen from the group comprising at least a belt, a mask, a helmet, a dressing, a pillow, and a mattress with a plurality of resonance media connected to the generator and secured in place in order to ensure uniformity of the constant, sinusoidal extremely low frequency current signal at a desired depth within the localized region and to avoid any interference or disturbance of the magnetic field.

10. The system of claim 1, wherein the system is used for regenerating cellular tissue composed of cells having keratin therein.

11. The system of claim 10, wherein the system is used for regenerating cellular tissue composed of cells having keratin therein for hair growth, to reduce wrinkles, skin creases, stretch marks and skin inelasticity.

12. The system of claim 1, wherein the system is used for vegetables.

13. The system of claim 1, wherein the system is used for repositories and cellular and tissue cultures laboratories.

14. A method for proliferation of stem cells grown in vitro in repositories or cellular cultures laboratories, by local application of the extremely low frequency magnetic field produced by the system of claim 1, the method comprising:
subjecting first sampled stem cells from a localized region to a first magnetic field by setting the generator to generate a first sinusoidal electric current signal having a first frequency chosen from the range between 7.65 Hz and 7.75 Hz;
subjecting second sampled stem cells from the same localized region to at least a second magnetic field by setting the generator to generate a second sinusoidal electric current signal having a second frequency chosen from the range between 7.65 Hz and 7.75 Hz, wherein the first and second frequencies are different;
determining a rate of cellular growth according to each of the frequencies to which the organic cells were subjected to;
selecting, between the first and second frequencies, an optimum frequency providing a highest rate of cellular growth Hz;
adjusting the generator to emit the electric current signal having only the optimum frequency; and
subjecting cellular cultures or cellular tissues grown in vitro to the optimum frequency of two hours per day over a minimum of 5 exposures.

15. The method according to claim 14, wherein the optimum frequency providing the highest rate of cellular growth is 7.69 Hz.

16. A method for proliferation of stem cells from any organic tissue in vivo in cellular tissue by local application of the extremely low frequency magnetic field produced by the system of claim 1, the method comprising:
establishing an anatomic depth, in a range of 1-100 mm of the stem cells within a localized region relative to the localized region's surface;
producing, with the generator, the constant, sinusoidal extremely low frequency current signal having the one predetermined frequency chosen from the range between 7.65 Hz and 7.75 Hz, and having one predetermined intensity adapted for said established anatomic depth;
subjecting the at least one resonance medium of the system to said constant, sinusoidal extremely low frequency current signal to yield a constant value magnetic field, measured at the emitter; and
atraumatically applying said magnetic field in said transverse direction to said localized region of the stem organic cells.

17. The method, according to claim 16, wherein the producing is for a predetermined period of at least two hours a day repeated on at least five occasions within at least 5 days.

18. The method of claim 16, wherein the established anatomic depth is 3 mm and the one predetermined frequency is 7.69 Hz.

* * * * *